US010149635B2

(12) United States Patent
Swiston et al.

(10) Patent No.: US 10,149,635 B2
(45) Date of Patent: Dec. 11, 2018

(54) INGESTIBLE DEVICES AND METHODS FOR PHYSIOLOGICAL STATUS MONITORING

(71) Applicant: MASSACHUSETTS INSTITUTE OF TECHNOLOGY, Cambridge, MA (US)

(72) Inventors: Albert Joseph Swiston, Cambridge, MA (US); Robert S. Langer, Newton, MA (US); Tadd Bernard Hughes, Andover, MA (US); Kerry Johnson, Somerville, MA (US); Carlo Giovanni Traverso, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 78 days.

(21) Appl. No.: 15/237,405

(22) Filed: Aug. 15, 2016

(65) Prior Publication Data

US 2017/0156632 A1 Jun. 8, 2017

Related U.S. Application Data

(60) Provisional application No. 62/205,064, filed on Aug. 14, 2015.

(51) Int. Cl.

*A61B 5/00* (2006.01)
*A61B 5/07* (2006.01)
(Continued)

(52) U.S. Cl.

CPC ............ *A61B 5/073* (2013.01); *A61B 5/0015* (2013.01); *A61B 5/0031* (2013.01);
(Continued)

(58) Field of Classification Search

CPC ...... A61B 2560/0223; A61B 2562/162; A61B 5/0015; A61B 5/02007; A61B 5/02055;
(Continued)

(56) References Cited

U.S. PATENT DOCUMENTS 3,971,362 A 7/1976 Pope et al.
8,842,497 B1 9/2014 Ruffa
(Continued)

OTHER PUBLICATIONS

Bowe, Liz, "High-Tech Yard Sale NASA holds conference to show off technology," *The Sun* [Baltimore, MD], 11D (Dec. 2, 1992).
(Continued)

*Primary Examiner* — George Manuel
(74) *Attorney, Agent, or Firm* — Smith Baluch LLP

(57) ABSTRACT

Reliable, real-time heart and respiratory rates are key vital signs used in evaluating the physiological status in many clinical and non-clinical settings. Measuring these vital signs generally requires superficial attachment of physically or logistically obtrusive sensors to subjects that may result in skin irritation or adversely influence subject performance. Given the broad acceptance of ingestible electronics, the approach disclosed here enables vital sign monitoring internally from the gastrointestinal tract. The large animal (porcine) experiments and a robust processing disclosed herein demonstrate the feasibility of this approach. Implementing vital sign monitoring as a stand-alone technology or in conjunction with other ingestible devices has the capacity to significantly aid telemedicine, optimize performance monitoring of athletes, military service members, and first-responders, as well as provide a facile method for rapid clinical evaluation and triage.

23 Claims, 20 Drawing Sheets

100
212
211
220
210
208
206
224
214
202
204

(51) Int. Cl.

| | |
|---|---|
| ***A61B 5/0205*** | (2006.01) |
| ***A61B 5/11*** | (2006.01) |
| ***A61B 7/02*** | (2006.01) |
| *A61B 5/02* | (2006.01) |
| *A61B 5/08* | (2006.01) |
| *A61B 8/02* | (2006.01) |

(52) U.S. Cl.

CPC ........ *A61B 5/0205* (2013.01); *A61B 5/02055* (2013.01); *A61B 5/11* (2013.01); *A61B 5/1107* (2013.01); *A61B 5/6861* (2013.01); *A61B 5/725* (2013.01); *A61B 5/7225* (2013.01); *A61B 5/7278* (2013.01); *A61B 5/7282* (2013.01); *A61B 7/023* (2013.01); *A61B 5/02007* (2013.01); *A61B 5/0816* (2013.01); *A61B 5/7207* (2013.01); *A61B 5/7257* (2013.01); *A61B 8/02* (2013.01); *A61B 2560/0214* (2013.01); *A61B 2560/0223* (2013.01); *A61B 2562/0204* (2013.01); *A61B 2562/0219* (2013.01); *A61B 2562/0247* (2013.01); *A61B 2562/06* (2013.01); *A61B 2562/162* (2013.01)

(58) Field of Classification Search

CPC ......... A61B 5/073; A61B 5/0816; A61B 5/11; A61B 5/1107; A61B 5/7225; A61B 5/7278; A61B 7/023; A61B 8/02

See application file for complete search history.

(56) References Cited

U.S. PATENT DOCUMENTS

| | | | | |
|---|---|---|---|---|
| 9,125,588 | B2 | 9/2015 | Parks et al. | |
| 2001/0051766 | A1* | 12/2001 | Gazdzinski ........ | A61B 1/00016 600/309 |
| 2002/0128542 | A1 | 9/2002 | Van Over | |
| 2004/0143182 | A1 | 7/2004 | Kucera et al. | |
| 2007/0027403 | A1 | 2/2007 | Swiston et al. | |
| 2007/0088194 | A1 | 4/2007 | Tahar et al. | |
| 2008/0228047 | A1 | 9/2008 | Parks et al. | |
| 2010/0036208 | A1 | 2/2010 | Koh et al. | |
| 2014/0309505 | A1* | 10/2014 | Euliano ................ | A61B 5/4833 600/302 |

OTHER PUBLICATIONS

Browning, C. et al., "Receiving, decoding and noise limiting systems for a new pressure-sensitive ingestible radio telemetric capsule," *Journal of Biomedical Engineering*, vol. 5 No. 3 pp. 262-266 (Jul. 1983).

Buller, M. et al., "Estimation of human core temperature from sequential heart rate observations," *Physiological Measurement*, vol. 34, No. 7, pp. 781-798 (Jul. 2013).

Chapon, P. et al., "Performance testing of an innovative telemetric temperature sensor in animals," *Journal of Thermal Biology*, vol. 37, No. 4, pp. 255-259 (Jul. 2012).

Cuddy, J.S. et al., "Hidalgo Equivital™ Physiological Monitor Product Review and Data Summary," *National Technical Information Service*, p. 27 (Dec. 2008).

Czyewski, Andrew "Smart pill containing microchip tracks adherence to medication," The Engineer Online (Jan. 19, 2012).

Harvey, D.G. et al., "Development of Breath-by-Breath Gas Exchange and Thermoregulatory Measurement Techniques for Use During Live Firefighting Training Drills," *Canadian Journal of Applied Physiology/Revue Canadienne de Physiologie Appliquee*, Suppl., vol. 30, p. S35 (2005).

Johannessen, E. et al., "Implementation of radiotelemetry in a lab-in-a-pill format," *Lab on a chip*, vol. 6, No. 1, pp. 39-45 (2006).

Kagamimori, S., "Studies on the Relationship between Daily Living Activities and Parameters Measured by an Ingestible Capsule Body Temperature-Sensor and Portable Body Movement-Heart Rate Monitors," *Journal of the Japanese Society of Balneology Climatology and Physical Medicine*, 72.1, p. 59-60 (Nov. 2008).

Kiourti, A. et al., "Implantable and ingestible medical devices with wireless telemetry functionalities: A review of current status and challenges," *Bioelectromagnetics* (Sep. 21, 2013).

Martinez, A. et al., "Ingestible pill for heart rate and core temperature measurement in cattle," *Annual International Conference of the IEEE Engineering in Medicine and Biology Society. IEEE Engineering in Medicine and Biology Society*, Conference vol. 1, pp. 3190-3193 (2006).

McKerracher, C., "Coming soon to a pill near you," *The Pipestone Flyer* [Millet, Alta] p. A.11 (Sep. 6, 2012).

"Medical Implants", Modern Plastics, p. 100, (May 1991).

Patents; Researchers Submit Patent Application, "Payment System for Wearable or Implantable Sensor Data", for Approval, *Marketing Weekly News*, p. 465 (Jul. 27, 2013).

Scott, S. et al., "Functional testing of the small and large bowel: The future," *CME Journal Gastroenterology, Hepatology and Nutrition*, vol. 8, No. 3, pp. 78-81 (2007).

Spanton, T., "Smile. These inventions will be with us by 2010," *The Sun* (London UK), p. 36. (Jul. 22, 2004).

"Sports Medicine; New Sports Medicine Study Findings Reported from United States Army Research Institute of Environmental Medicine," Health & Medicine Week, p. 2280 (2012).

"Subjects swallow space-age monitors," Science News, p. 106 (Feb. 13, 1988).

Swain, P., "The future of wireless capsule endoscopy," *World Journal of Gastroenterology*, vol. 14, No. 26, pp. 4142-4145 (2008).

Traverso., G, et al., "Physiologic Status Monitoring via the Gastrointestinal Tract," PLoS One 10(11): e0141666 (Nov. 18, 2015). doi:10.1371/journal.pone.0141666.

Yokota, M. et al., "Applications of real-time thermoregulatory models to occupational heat stress: Validation with military and civilian field studies," *Journal of Strength and Conditioning Research*, vol. 26., Suppl. 2, pp. S37-S44 (Jul. 2012).

Zarate, N. et al., "Accurate localization of a fall in pH within the ileocecal region: Validation using a dual-scintigraphic technique," *American Journal of Physiology—Gastrointestinal and Liver Physiology*, vol. 299, No. 6, pp. G1276-G1286 (Dec. 2010).

International Search Report and Written Opinion dated May 12, 2017 from International Application No. PCT/US2016/047047, 21 pages.

* cited by examiner

INGESTIBLE DEVICES AND METHODS FOR PHYSIOLOGICAL STATUS MONITORING

CROSS-REFERENCE TO RELATED APPLICATION(S)

This application claims the priority benefit, under 35 U.S.C. § 119(e), of U.S. Provisional Patent Application Ser. No. 62/205,064, entitled "Ingestible Devices and Methods For Physiological Status Monitoring," filed on Aug. 14, 2015, the disclosure of which is incorporated herein by reference in its entirety.

GOVERNMENT SUPPORT

This invention was made with Government support under Grant No. R37 EB000244 awarded by the National Institutes of Health and under Contract No. FA8721-05-C-0002 awarded by the U.S. Air Force. The Government has certain rights in the invention.

BACKGROUND

Non-obtrusive, real-time physiological monitoring would be beneficial in civilian health care settings, in athletes, and operationally in military or civilian service members. Knowing an individual's physiological status can lead to targeted preventative interventions, improved performance, risk mitigation in dangerous contexts and immediate monitoring following injury or illness. Current physiological monitoring systems are capable of measuring a host of useful physiological parameters such as heart rate (HR), core temperature (Tc), and breathing rate (BR); however, these systems suffer from limited operational utility due to ergonomic obtrusiveness (wearing a harness, for instance), limited battery life, and poor signal fidelity during movement.

HR and BR are essential vital signs used in the evaluation of the physiologic status of children and adults in clinical and non-clinical settings. They constitute the initial measurements in acutely ill patients and provide the basis for clinical severity stratification as well as markers of response to life-saving cardiopulmonary resuscitation. Additionally, HR and BR serve as non-diagnostic indicators of performance status in service members and in performance athletes.

There are numerous methods for monitoring HR and BR, but most require the attachment of superficial sensors to the body. HR can be monitored using electrical methods such as electrocardiogram (ECG), optical methods such as photoplethysmography (PPG) (pulse oximetry), or mechanical methods such as ballistocardiography. BR can be monitored directly using trans-thoracic plethysmography and expired gas analysis approaches, or indirectly using advanced processing methods such as PPG. All of these methods have some limitations, as they may cause patient discomfort, skin irritation, and they cannot be used reliably in high-physical activity contexts where motion artifacts may corrupt the signal. Over the last decade, ingestible medical devices have gained broad acceptance; for example, ingestible devices can measure pH, and video capsule endoscopy is widely used for diagnosis of gastrointestinal (GI) pathology. Vital sign monitoring from within the GI tract may be a safe and effective alternative to existing clinical monitoring systems.

SUMMARY

Embodiments of the present invention include an ingestible physiological status monitoring (PSM) device that uses a signal processing flow to determine heart rate (HR), core temperature (Tc), and breathing rate (BR) from signals acquired by an analog front end. For instance, an example device can measure signatures everywhere in the gastrointestinal (GI) tract from the esophagus to the duodenum, both with and without tissue contact. An exemplary device can operate at low power with relatively long battery life. For example, it could operate a power budget shows continuous operation at maximum current draws of 4 days using a mercury-free, silver oxide based power source. This would satisfy longevity requirements for a nonpersistent device, and may even fulfill requirements for a persistent one.

A PSM pill may facilitate rapid acquisition of physiologic status information, and has broad applicability in both public and private sectors. Given that acquiring vital signs is part of standard medical practice, such a device would have a clear role in areas and scenarios where rapid monitoring deployment is needed. For example, these include emergency medical technician (EMT) field assessments of patients, patients awaiting care at an emergency department and home monitoring of vital signs. Other commercial interest would include recreational uses, such as for athletes, where our device obviates the need for a wearable rectal thermometry probe and has a significant comfort advantage. Public sector uses would include military populations, as well as for first responders such as fire and police services. In short, applications for this device include, but are not limited to: (1) medical (clinical diagnostic); (2) safety monitoring devices, for instance measuring Tc in first responders; (3) sport/recreational monitoring (e.g., in performance athletes); and (4) battlefield monitoring for military personnel (operational safety and monitoring).

Additional embodiments of the present invention include ingestible devices and methods for monitoring a physiological status of a mammal. An example ingestible device may include a biocompatible housing, an acoustic sensor disposed within the biocompatible housing, an analog-to-digital converter (ADC) disposed within the biocompatible housing and operably coupled to the acoustic sensor, a processing unit disposed within the biocompatible housing and operably coupled to the ADC, a radio disposed within the biocompatible housing and operably coupled to the processing unit, and a power supply. In operation, the acoustic sensor transduces acoustic waves propagating within the mammal into an analog signal. The ADC generates a digital representation of the analog signal. The processing unit stores the digital representation in a memory. The radio transmits the digital representation to a base station disposed outside the mammal. And the power supply provides electrical power to the acoustic sensor, the ADC, the processing unit, and the radio.

The ingestible device's biocompatible housing may have an acoustic impedance of about 2 Mrayls to about 20 Mrayls. It may also have a length of less than about 3 cm (e.g., 2 cm or less) and a diameter of less than about 1 cm.

The acoustic sensor may sense acoustic events within a range of about 5 Hz and about 10 kHz. The processing unit may form an estimate of a heart rate of the mammal, an estimate of a breathing rate of the mammal, or an indication of a pathological event of the mammal based on the digital representation of these acoustic events.

The radio may transmit the digital representation to the base station and receive a signal from the base station. In some cases, the processing unit triggers data collection by the acoustic sensor in response to the signal from the base station.

Examples of the ingestible device may also include a low-pass filter disposed within the biocompatible housing and operably coupled to the acoustic sensor and the ADC. This low-pass filter filters the analog signal prior to generation of the digital representation of the analog signal. And the processing unit estimates a breathing rate of the mammal based on the digital representation.

Examples of the ingestible device may also include a band-pass filter disposed within the biocompatible housing and operably coupled to the acoustic sensor and the ADC. In operation, the band-pass filter filters the analog signal prior to generation of the digital representation of the analog signal. The processing unit estimates a heart rate, heart rhythm, or both based on the digital representation.

The ingestible device may include other sensors as well, including a temperature sensor, accelerometer, and pressure sensor, each of which may disposed within the biocompatible housing and operably coupled to the processing unit. In operation, the temperature sensor senses a temperature of the mammal. The accelerometer senses acceleration of the ingestible device and provides an acceleration signal representative of the acceleration of the ingestible device to the processing unit. The processing unit may be configured to estimate motion of the ingestible device, motion of the mammal, or both based on the acceleration signal. The pressure sensor senses a change in pressure relating to motion separation, smooth muscle functionality, gastrointestinal transit time, or an inflammatory condition.

In some examples, the processing unit may estimate the heart rate, breathing rate, or indication of the pathological event by subsampling the digital representation to produce a subsampled digital representation, generating a spectrogram of the subsampled digital representation, producing a modulation transform of the spectrogram, and analyzing a distribution of energy in the modulation transform. In other examples, the processing unit may estimate the indication of the pathological by filtering the analog signal or the digital representation with a matched filter corresponding to an acoustic signature of the pathological event, which could be a cardiac arrhythmia, stenosis, chronic obstructive pulmonary disease, or asthma. The radio may transmit an indication of the pathological event to a receiver disposed outside of the mammal.

Another exemplary ingestible device includes a biocompatible dielectric material having an acoustic impedance of about 2 Mrayls to about 20 Mrayls; a hydrophone encapsulated within the biocompatible dielectric material; first and second filters operably coupled to the hydrophone; first and second ADCs operably coupled the first and second filters, respectively; a processor operably coupled to the first and second ADCs; and a radio operably coupled to the processor. In operation, the hydrophone acquires acoustic data within a frequency range of about 5 Hz to about 10 kHz. The first and second filters generate first and second filtered analog signals from the acoustic data. The first and second ADCs generate first and second digital signals from the first and second filtered analog signals, respectively. The processor estimates a heart rate of the mammal from the first digital signal and a breathing rate of the mammal from the second digital signal. And the radio transmits the heart rate and the breathing rate to an external wireless device disposed outside the mammal power supply.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1A:
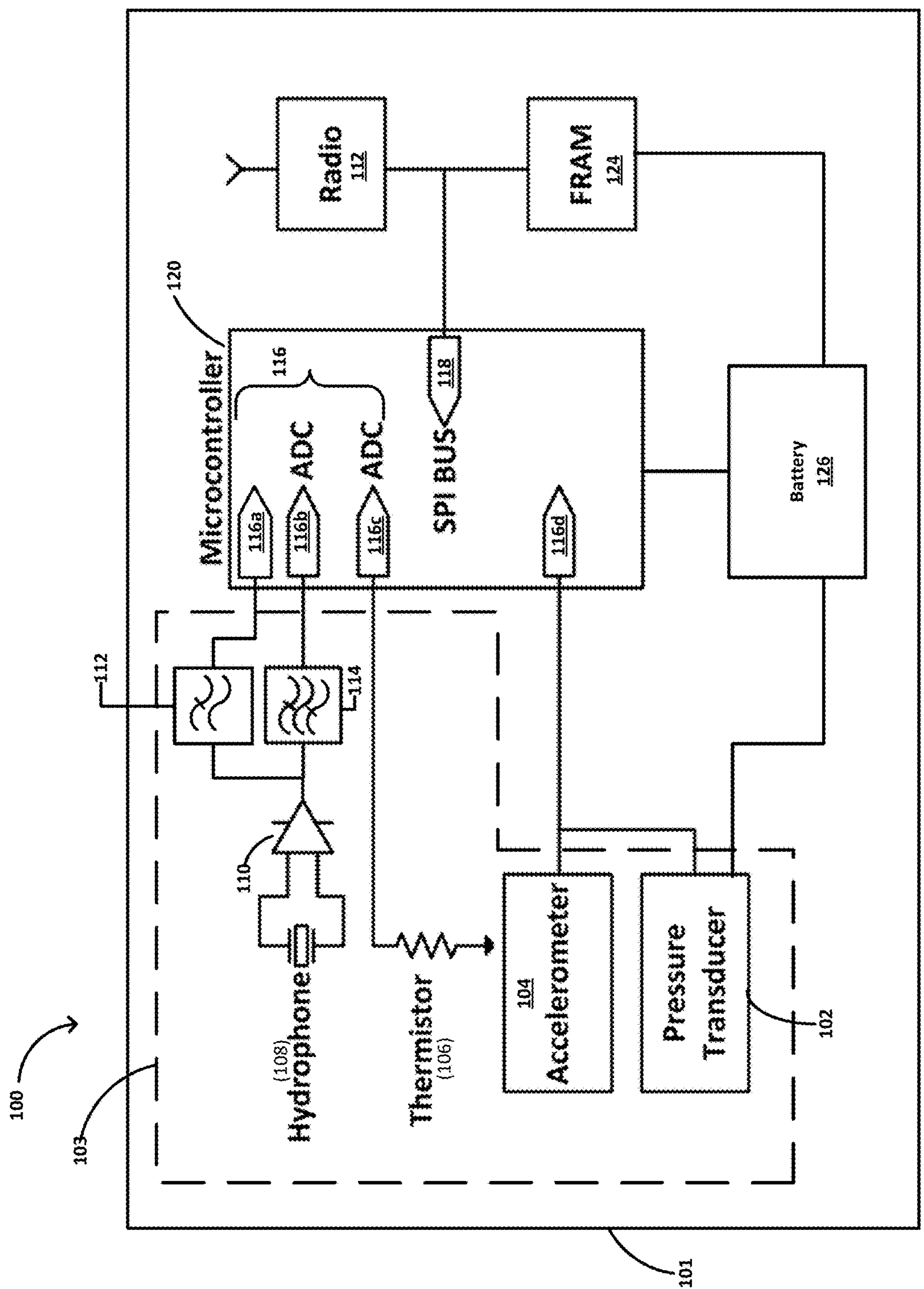
FIG. 1A is a schematic of an ingestible physiological monitoring device.

Physiological status monitoring is central to the clinical evaluation of patients and increasingly used in non-clinical settings for safety (for example, military service members and first-responders) and performance monitoring (such as professional athletes). Though significant development has focused on low-profile external vital sign monitoring systems, extended monitoring in non-wearable formats has seen little development. Wearable systems can be associated with skin irritation from allergic responses or repetitive abrasion during extended use in high physical activity settings, as well as from constriction, and all are subject to the logistical burdens of user compliance. Furthermore, wearable systems are not always capable of directly measuring some key physiological variables externally, namely core temperature.

Ingestible devices, on the other hand, have a number of advantages over wearable systems. The ergonomic profile of an ingestible-sized device is minimal; unless a patient has a specific contra-indication for such a device (bowel obstruction, etc.), the user may remain asymptomatic for the duration of monitoring. Such small devices may be similar in size to a bolus of food and will remain free-floating in the GI tract; with an appropriate material choice for the device capsule, this may reduce or minimize abrasive irritation of the GI mucosa. Furthermore, ingestible electronic systems offer the possibility for in vivo, yet non-implantable medical devices able to monitor difficult-to-measure variables (such as core temperature) simultaneously with HR and BR.

Embodiments of the present invention include an unobtrusive physiological monitoring device capable of measuring heart rate, breathing rate, and core temperature in an ingestibly-sized package. An example device measures relies on acoustic signatures of heart and lung activity, and includes a simple thermistor temperature measurement component. A processor communicatively coupled or within the device implements an algorithm process flow that pulls out physiological parameters from noisy signals (that is, corrupted by motion or other interference). For example, the process flow can be executed using one or more on-board extremely low-power processing units (such as a Texas Instrument microcontroller). Given the elegance of collecting the acoustic signals and the digital processing back-end, an exemplary device could be produced relatively inexpensively and can be used as both a transient (e.g., is voided normally) or persistent device (e.g., the device may be affixed somewhere along the GI tract for measurement over several days or weeks).

Example physiological monitoring devices can be ingested and used to sense vital signs in a heterogeneous set of environments in the gastrointestinal (GI) tract using a single sensing modality. They can be used in vivo at various locations along the GI tract both in the presence and absence of food material. Signal fidelity is maintained with and without microphone tissue contact, as well as within solid and liquid food material. More specifically, they can be used to measure heart rate and breathing rate and to diagnose cardiac murmurs and respiratory pathology:

Monitoring of Heart Rate. An ingestible physiologic status monitoring device can be ingested or placed in the oral cavity of a subject and immediately start collecting HR. The HR can be captured throughout the GI tract in both the fasting and fed state. HR is one of the basic physiologic parameters evaluated in clinical settings, on the battlefield and in sport for performance output. It can be applied to indicate hydration status, sepsis, arrhythmias as well as optimal performance status in the field. For instance, excellent correlations between HR and metabolic output and core temperature have been shown previously.

Monitoring of the Breathing Rate. An ingestible physiologic status monitoring device can be ingested or placed in the oral cavity of a subject and immediately start collecting the BR. The BR can be captured throughout the GI tract in both the fasting and fed state. The BR is one of the basic physiologic parameters evaluated in clinical settings. BR has the capacity to help inform the user and team of oxygenation status, fatigue, and anxiety. Clinically, it can help in the evaluation of respiratory conditions and their response to treatment (e.g., asthma, COPD, pneumonia). BR has been shown to be an important variable in military contexts for indicating fatigue and work rates.

Acoustic diagnosis of cardiac murmurs. An ingestible physiologic status monitoring device can enable the extended recording and analysis of the full cardiac cycle from an acoustic perspective in a minimally invasive fashion. The acoustic signal can be analyzed for the presence of cardiac murmurs, which can help delineate the presence of cardiac valvular pathology. Conditions such as aortic stenosis, mitral regurgitation, and hypertrophy each have characteristic acoustic signatures that may be automatically identified through analysis of the S1 and S2 waveforms, e.g., as described in http://circ.ahajournals.org/content/113/9/1255.short, which is incorporated herein by reference in its entirety.

Acoustic diagnosis of respiratory pathology. An ingestible physiologic status monitoring device can selectively analyze varying portions of the acoustic spectrum and thereby aid in the management of chronic respiratory illness. For example, early acoustic detection of wheeze in a patient suffering from asthma may signal an earlier use of a bronchodilator (e.g. albuterol) and/or inhaled steroid.

Electrical and Functional Aspects of a Physiological Monitoring Device

FIG. 1A is a schematic illustration of a physiological monitoring device 100. The physiological monitoring device 100 includes an analog front end 103 disposed within a biocompatible housing 101. The analog front end 103 comprises a thermistor 106, acoustic sensor (here, a hydrophone 108), accelerometer 104 pressure transducer 102, high-impedance amplifier 110, optional first filter 112 (e.g., a low-pass filter (LPF)), and second filter 114 (e.g., a band-pass filter (BPF)). The output of the hydrophone 108 is coupled to the input of the amplifier 110, and the output of the amplifier 110 is coupled to the inputs of the LPF 112 and the BPF 114.

The physiological monitoring device 100 also includes a processing unit, shown here as a microcontroller 120, that is coupled to the outputs of the LPF 112, BPF 114, accelerometer 104, and pressure transducer 102. The microcontroller 120 comprises a plurality of 12-bit analog-to-digital converters (ADCs) 116*a*, 116*b*, 116*c*, and 116*d* (collectively, ADCs 116) and a Serial Parallel Interface (SPI) bus 118. (As understood by those of skill in the art, the ADCs 116 can also be implemented as discrete components separate from the microcontroller 120.) The ADCs 116*a*, 116*b*, and 116*c* are electrically coupled to the outputs of the LPF 112, the BPF 114, and the thermistor 106, respectively. The other ADC 116*d* is connected to both the accelerometer 104 and the pressure transducer 102. The SPI bus 118 is coupled to a radio 122 and a memory, shown in FIG. 1A as a Ferroelectric Random Access Memory (FRAM) 124.

The processing circuitry may include any suitable microcontroller, field-programmable gate array (FPA), or other processing device. In this case, the microcontroller 120 comprises a 32 MHz ARM Cortex-M3 central processor unit (CPU), a 256 Kbyte flash memory, a 32 Kbyte Static Random Access Memory (SRAM), a Direct Memory Access (DMA) controller, 16 external interrupts, and an internal oscillator. It draws a standby current of 1.15 μA standby and has a 1.65-3.6 V operating range. It fits on a 4.2×3.2 $mm^2$ bare die micro ball grid array, including the ADCs 116 and SPI interfaces 118.

The FRAM 124 is a non-volatile random access memory that stores data acquired by the sensors and instructions to be executed by the microcontroller 120. It retains data even when the physiological monitoring device 100 is not powered. In some embodiments, the data in FRAM 124 is electrically erased and is reprogrammed to provide functionality similar to a flash memory.

The radio 122 that includes a Radio Frequency (RF) transceiver module, which encodes messages for transmission and decodes received messages, and an antenna for transmitting and receiving messages. In operation, the radio 122 provides one-way or two-way communication with an external base station 140, such as a laptop computer, a desktop computer, a smartphone, or a medical device with another radio or connection to a wireless network.

Typically, the radio 122 may be configured to operate in the Medical Implantable Communication Services Band (MICS, 402-405 MHz). The radio 122 comprises tunable capacitors on RF inputs for dynamic tuning, antenna, and crystal and decoupling capacitors. In one example, it draws an average current of 290 nA in wake-up mode at 1 second intervals and 5.3 mA in transmit mode. It can transmit coded data at a rate of 134-515 kbps with a 2.0-3.5 V operating range. It may occupy relatively little space, e.g., 4.2×3.0 $mm^2$ bare die micro ball grid array.

The electronic components disclosed above are coupled together to a battery 126 that powers the physiological monitoring device 100. The battery 126 may comprise one or more biocompatible battery cells, such as silver oxide, zinc-air, and alkaline battery cells, that provide enough power for the device 100 to operate for hours or days, depending on the power consumption of the electronic components. To extend battery life, the microcontroller 120 may turn the one or more of the electronic components off when not in use or operate them in a low-power or dormant mode when the device 100 is not collecting data. It may also selectively reduce the sampling rate of the ADCs 116, transmit via the radio 122 in periodic bursts, etc., in order to reduce power consumption.

In some embodiments, the biocompatible housing 101 comprises an encapsulant made of silicone or another suitable biocompatible material. The electronic components disclosed above are coupled together electronically and mechanically as disclosed below, then dipped or coated with the silicone. The silicone hardens to form the housing 101. In other embodiments, the biocompatible housing 101 comprises one or more pieces that are mated together around the electronic components to protect them. In embodiments with a housing formed of one or more pieces, the hydrophone 108 may be acoustically mated to an inner surface of the biocompatible housing 101 in order to reduce acoustic reflections at the interface between the hydrophone 108 and the biocompatible housing 101. In these cases, the housing 101 and hydrophone 108 may be mated together with media whose acoustic impedance approximately matches the acoustic impedance of water.

The biocompatible housing 101 may be small enough for a mammal to swallow comfortably. For use by an adult human, the biocompatible housing 101 may be less than about 3 cm long (e.g., 2.5 cm, 2.0 cm, 1.5 cm, or 1.0 cm long) and has a diameter of less than about 1 cm (e.g., 0.9 cm, 0.8 cm, 0.7 cm, 0.6 cm, or 0.5 cm).

The hydrophone 108 measures acoustic signatures in order to determine heart rate and breathing rate. The hydrophone 108 may comprise a metallized piezoelectric material backed by a compressible medium, such as air, biocompatible polymer, oil, or foam. The compressible medium allows for external pressure to deform the piezoelectric material. Strain in the piezoelectric material generates an electric charge whose amplitude is proportional to the amplitude of the acoustic waves deforming the piezoelectric material. The hydrophone 108 thus transduces acoustic waves into analog signals. This electric charge is sent to an amplifier 110, which amplifies the analog signal as well understood in the art. (If the amplifier 110 is implemented as a CMOS op amps, it may provide high impedance, but leakage current into hydrophone 108 capacitance may rail out the amplifier 110. To prevent this problem, the device 100 may include a servo loop to cancel the leakage current.)

In the embodiment shown in FIG. 1A, the amplifier 110 is electrically connected to the LPF 112 and BPF 114. In this case, the LPF 112 and BPF 114 are passive topology RC-type filters that are tuned during fabrication. In some embodiments, the LPF 112 and BPF 114 are active topology RC-type filters that are tuned dynamically. In still other embodiments, the LPF 112 and BPF 114 are filtered in the digital domain. Tunable filters, such as active topology RC-type filters and digital filters, can be adjusted to reduce motion artifacts and noise, to pass information for diagnosing different medical conditions, or both.

The LPF 112 and BPF 114 shown in FIG. 1A are analog filters that process analog signals in a frequency-dependent manner. More specifically, the LPF 112 filters the amplified analog signal from the amplifier 110 by passing signals with a frequency lower than a cutoff frequency and attenuating signals with frequencies higher than the cutoff frequency. Typically, the cutoff frequency of the LPF 112 is chosen to be about 3 Hz with a 6 dB/octave rolloff. At this cutoff frequency, the LPF 112 provides filtered data from which the breathing rate can be determined. Similarly, the BPF 114 passes electrical signals with frequencies within a particular range (called the "passband") and attenuates electrical signals with frequencies outside that range. For instance, the BPF 114 may have a passband of about 30 Hz to about 60 Hz with a 6 dB/octave rolloff. With this passband, the BPF 114 provides filtered data from which the heart rate can be determined.

Those of skill in the art will appreciate that any cutoff frequency, passband, and rolloff that allow for separation of frequencies to be observed can be chosen. For instance, the filter frequencies may be chosen separate heart sounds (<100 Hz) from lung sounds (100-1000 Hz). More specifically, the LPF 112 may have a cutoff frequency of about 100 Hz and the BPF 114 may have a passband of about 100-1000 Hz. At these values, the data from the LPF 112 and BPF 114 may be used to diagnose other clinical conditions, including a cardiac arrhythmia, stenosis, chronic obstructive pulmonary disease, or asthma. Likewise, to detect subtler clinical conditions, such as heart arrhythmias, the rolloff may be 12 dB/octave or 24 dB/octave.

Other embodiments of the physiological monitoring device 100 may use different numbers, combinations, and types of filters. For instance, another embodiment may use a high-pass filter instead of the BPF 114, a bandpass filter with an appropriate passband instead of the LPF 112, or both. The BPF 114 can also be implemented as a matched filter whose passbands is matched to the acoustic signature of a pathological event, such as a cardiac arrhythmia, stenosis, chronic obstructive pulmonary disease, or asthma.

Filtering can also be implemented digitally with the microcontroller 120 instead of with discrete analog components like the LPF 112 and BPF 114. Digital filtering offers more flexibility because the cutoff frequencies and passbands can be reprogrammed remotely, e.g., to screen for different pathological events or conditions, but consumes more power than analog filtering with passive components like the LPF 112 and BPF 114, which don't consume any power.

In some embodiments, the thermistor 106 is used to measure core body temperature. As understood in the art, the thermistor 106 is an electrical resistor that changes resistance with change in temperature. The ADC 116*c* is connected to the thermistor 106 to sample these changes in resistance. The microcontroller 120 stores these samples in the FRAM 124. The resistance values may be calibrated against actual temperature a priori with the results stored in the FRAM 124. In some cases, the microcontroller 120 also correlates the resistance changes with the mammal's core temperature and stores the mammal's core temperature in the FRAM 124 and/or transmits the core temperature to an external base station via the radio 122.

The accelerometer 104 is used to measure acceleration of the physiological monitoring device 100. This acceleration may be caused by movement of the physiological monitoring device 100 within the mammal's gastrointestinal tract, movement of the mammal, or both. In any of these cases, the accelerometer 104 produces an acceleration signal that the microcontroller 120 stores in the FRAM 124. In some cases, the microcontroller 120 estimates the motion of the physiological monitoring device 100, the mammal, or both from the acceleration signal and/or transmits the motion estimate(s) to an external base station via the radio 122.

The pressure transducer 102 samples intralumen pressure in the GI tract and generates electrical signal as a function of the measured pressure. The resulting electrical signal is digitized by the ADC 116*d* and written to the FRAM 124 by the microcontroller 120. The pressure sensed by the pressure transducer 102 represents motion separation, smooth muscle functionality, GI transit time and for diagnosis of inflammatory conditions, such as colitis and Crohn's disease.

As shown in FIG. 1A, the microcontroller 120 is electrically connected to and receives signals from the BPF 114, LPF 112, thermistor 106, accelerometer 104 and the pressure transducer 102. In some cases, the microcontroller 120 simply controls the ADCs 116, e.g., by switching them on to sample analog data from the hydrophone 108, thermistor 106, and accelerometer 104, moving the sampled (digitized) data into the FRAM cache 124 periodically, and then turning off the ADCs 116. In such an implementation, the microcontroller 120 may switch all of the ADCs 116 on and off simultaneously, at different frequencies, or at different times.

The sampling rates of the ADCs 116 may be chosen based on the frequencies of the signals being digitized and the desired power consumption. For instance, the ADC 116*a* coupled to the LPF 112 may have a sampling rate of two to ten times the cutoff frequency of the LPF 112 (e.g., 6 Hz to 1 kHz). Likewise, the ADC 116*b* coupled to the BPF 114 may have a sampling rate of two to ten times the high frequency edge of the passband (e.g., 80 Hz to 10 kHz). Generally speaking, operating the ADCs 116 at lower sampling rates uses less power.

In other implementations, the microcontroller 120 may perform some or all of the autocorrelation signal processing of the digitized in real time or on demand to reduce power consumption by the radio, to free up memory, or both. (The unprocessed data is typically more voluminous than the processed data and therefore takes longer to transmit and occupies more memory.) For instance, the microcontroller 120 may convert the time domain digitized signals into frequency domain signals using a Fast Fourier Transform (FFT) or another suitable processing technique to derive the mammal's heart rate, breathing rate, temperature, pressure, and acceleration data as explained in greater detail below. In some of these implementations, the microcontroller 120 may store and transmit both the raw and processed data, store the raw data and transmit the processed data, or store and transmit the processed data.

The microcontroller 120 transmits the stored and/or processed data to an external base station 140 via SPI bus 118, which is connected to the radio 122 and FRAM 124. The microcontroller 120 may transmit information via the radio 122 to the base station 140 at regular or predetermined intervals or in response to commands from the base station. The microcontroller 120 may also receive and process other commands from the base station 140, including commands to start collecting data, stop collecting data, process the data, provide a status report, etc. The microcontroller 120 may also transmit messages to the base station via the radio 122, including status reports indicating battery power, location, malfunctions, etc.

Figure 1B:
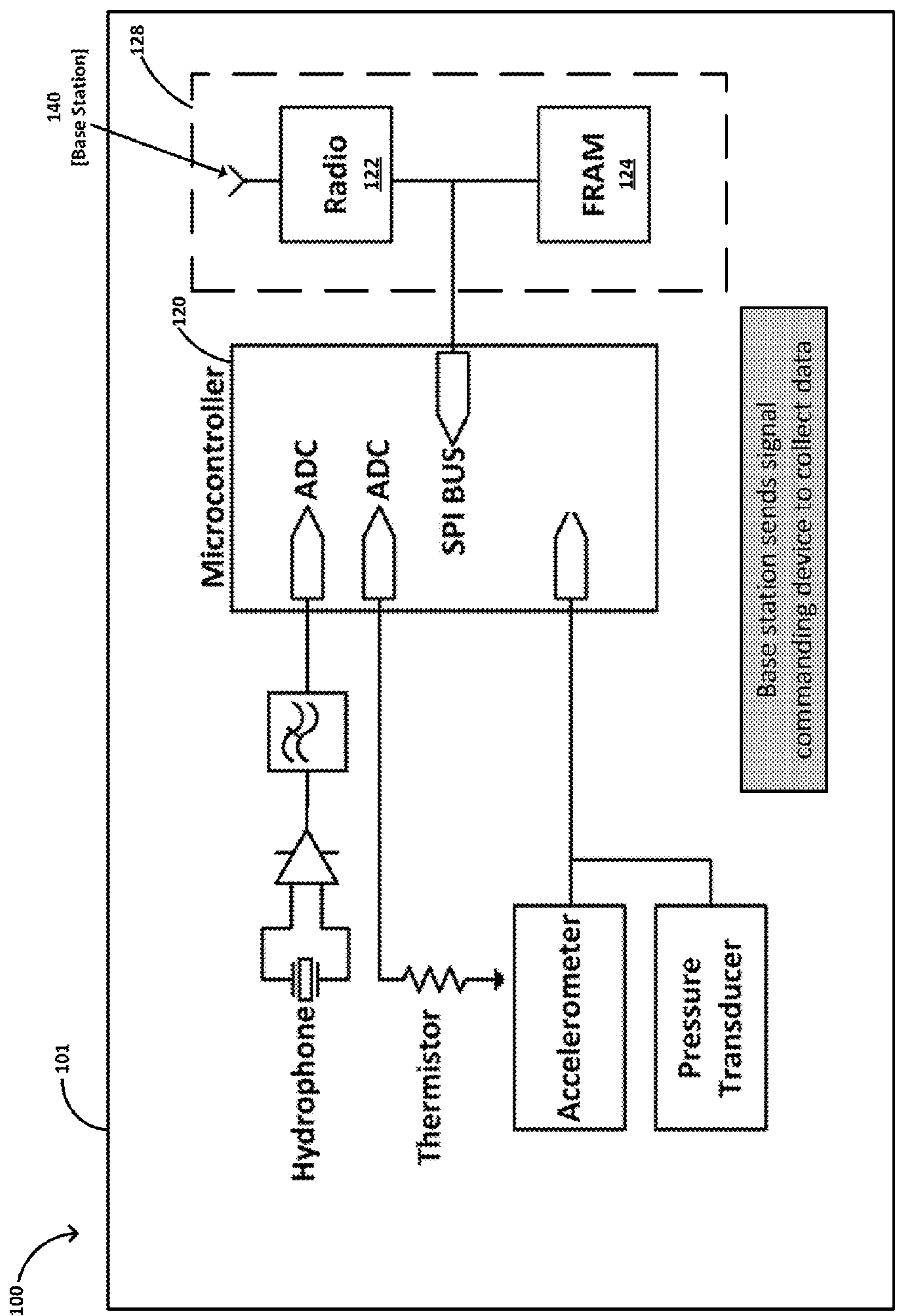
FIGS. 1B-1D illustrate operation of the ingestible physiological monitoring device of FIG. 1A.
Figure 1C:
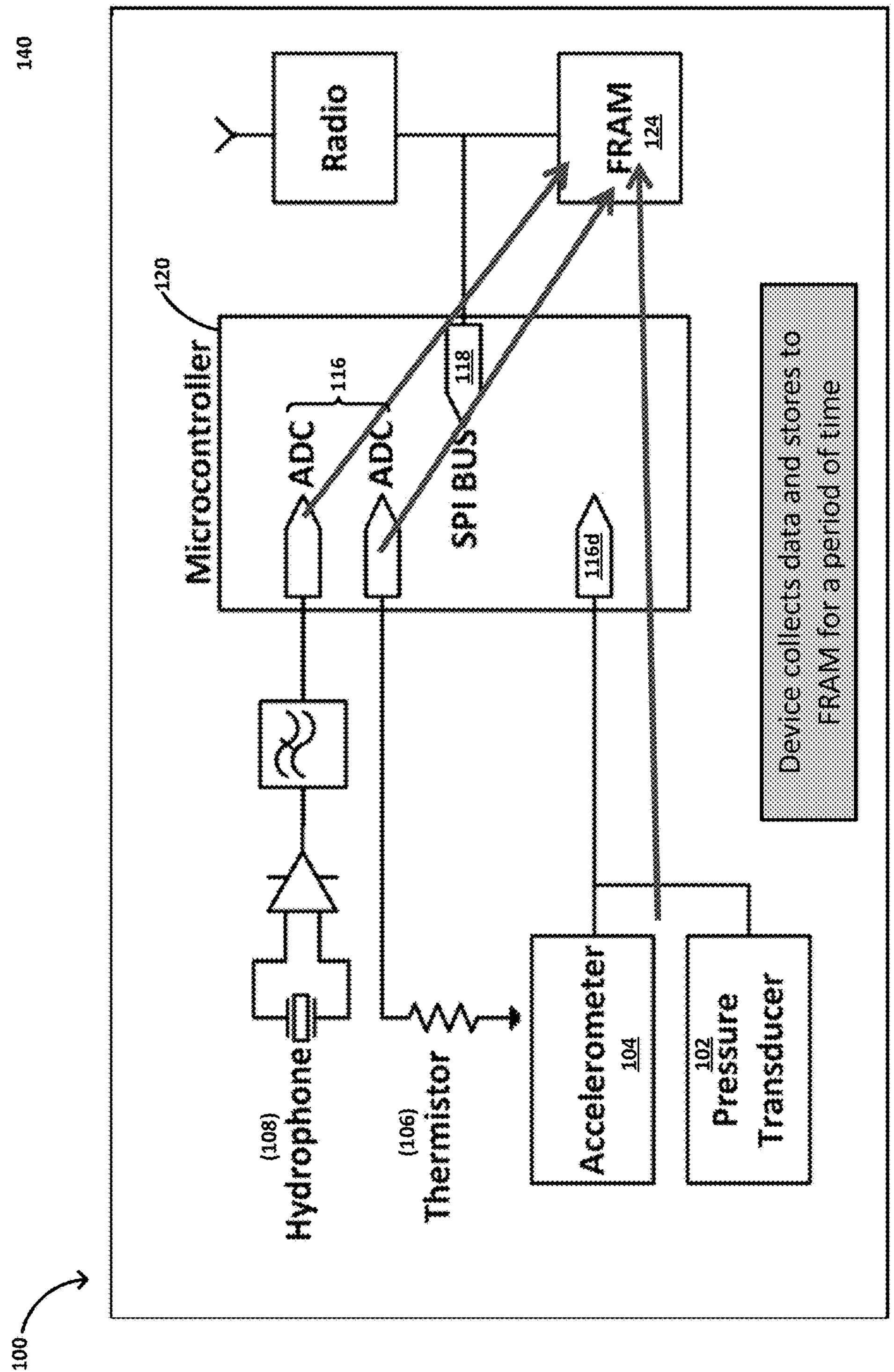
Figure 1D:
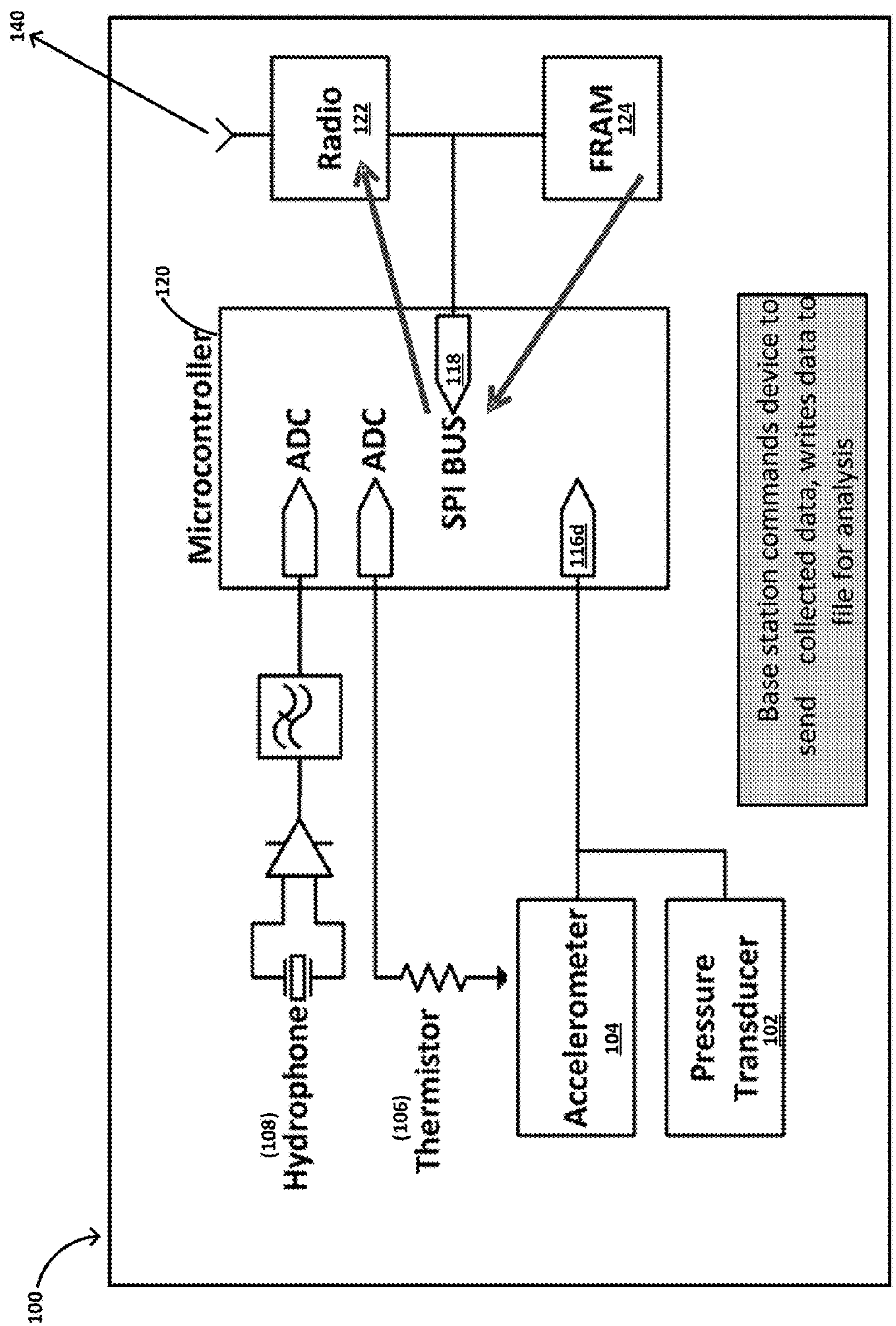

FIGS. 1B, 1C, and 1D depict the working of the physiological monitoring device 100 shown in FIG. 1A. Referring to FIG. 1B, the radio 122 receives one or more command signals from a base station 140 and provides the command signals to the microcontroller 120. The radio 122 converts the command signals received from the base station 140 into electrical signals that are compatible with the physiological monitoring device 100.

Referring to FIG. 1C, in response to receiving the command signals from the base station 140, the physiological monitoring device 100 collects, processes, and stores data representing the mammal's breathing rate, heart rate, core temperature, acceleration, and pressure using the sensors described above. These signals are filtered and received by the microcontroller 120, which digitizes them and optionally analyzes them to determine heart rate, breathing rate, and/or other pathological events. The microcontroller 120 stores the raw and/or processed data in the FRAM 124.

Referring to FIG. 1D, the base station 140 commands the physiological monitoring device 100 to transmit the collected data. The microcontroller 120 responds to this command by transmitting the raw and/or processed data to the base station via the radio 122. The base station 140 receives the raw and/or processed data, stores it in memory, and analyzes it against threshold or historic data to generate insights as to the mammal's physiological status. For instance, the analyzed data may be used to monitor the body and generate alerts if the data indicates a pathological event, such as a cardiac arrhythmia, stenosis, chronic obstructive pulmonary disease, or asthma.

Mechanical and Acoustic Aspects of a Physiological Monitoring Device

Figure 2A:
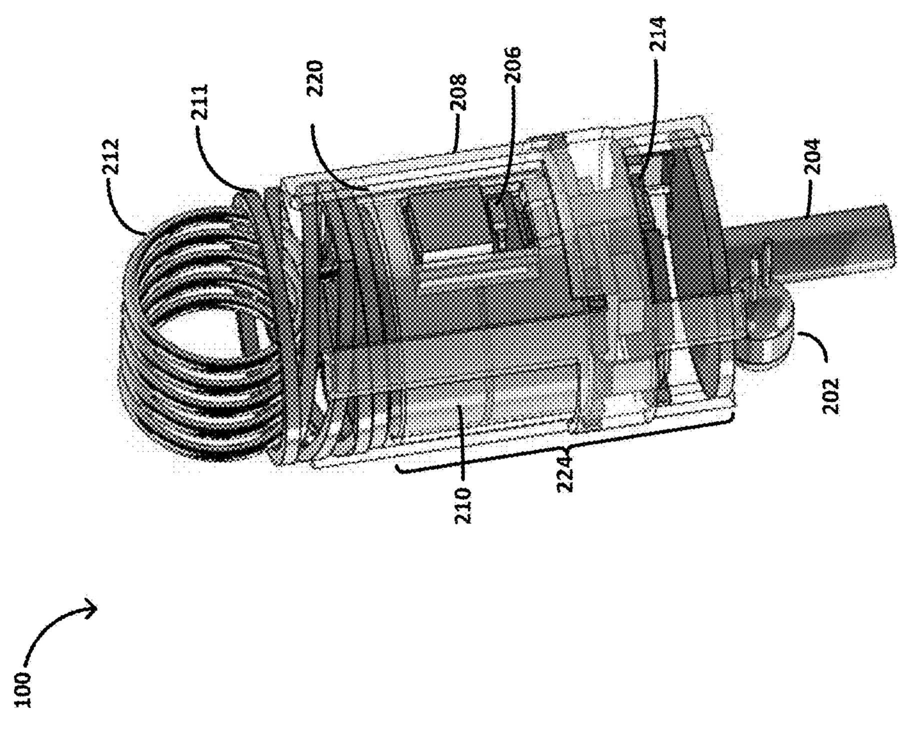
FIGS. 2A and 2B are perspective views of an ingestible physiological monitoring device.
Figure 2B:
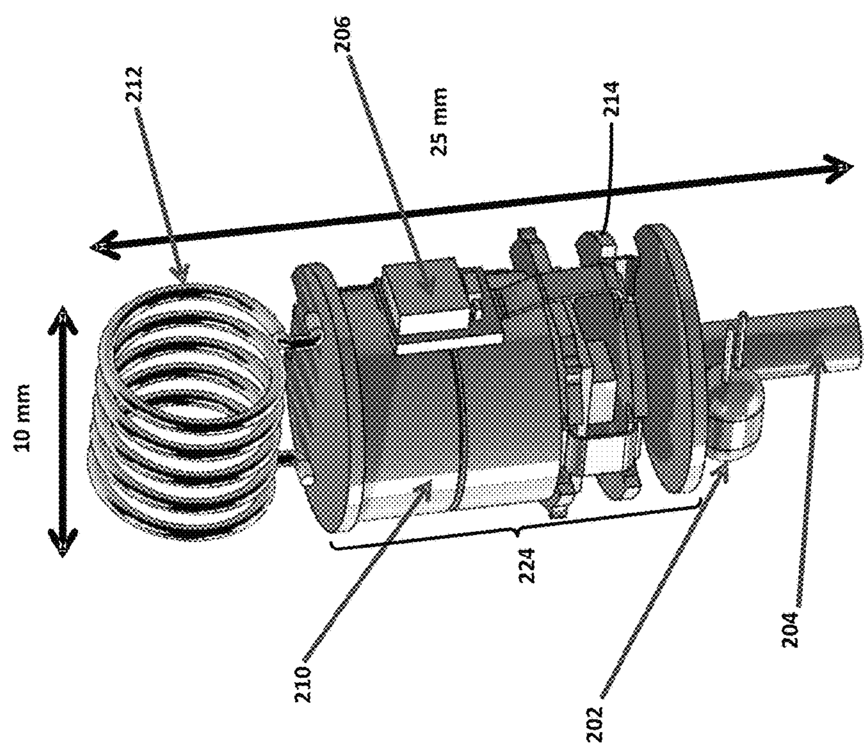
Figure 2C:
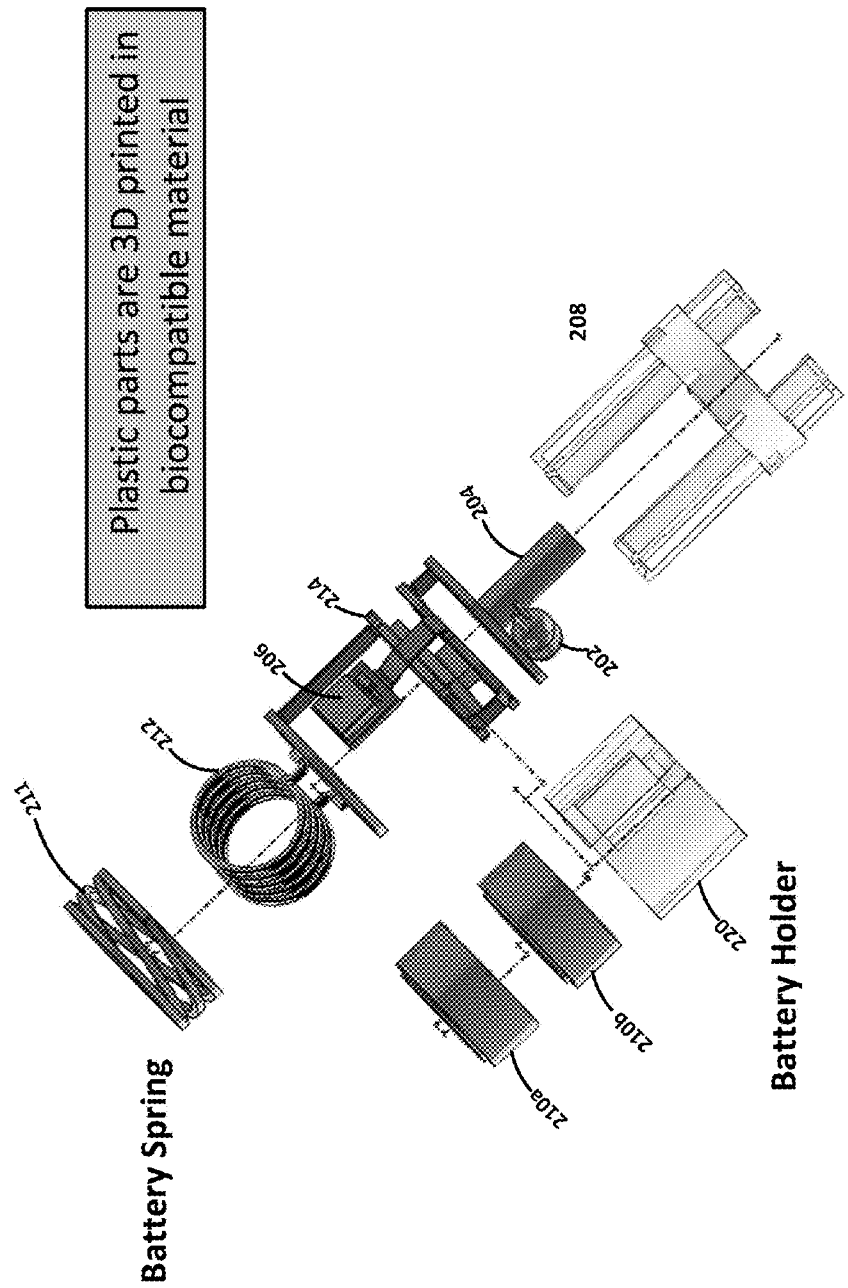
FIG. 2C is an exploded view of the ingestible physiological monitoring device of FIGS. 2A and 2B.
Figure 2D:
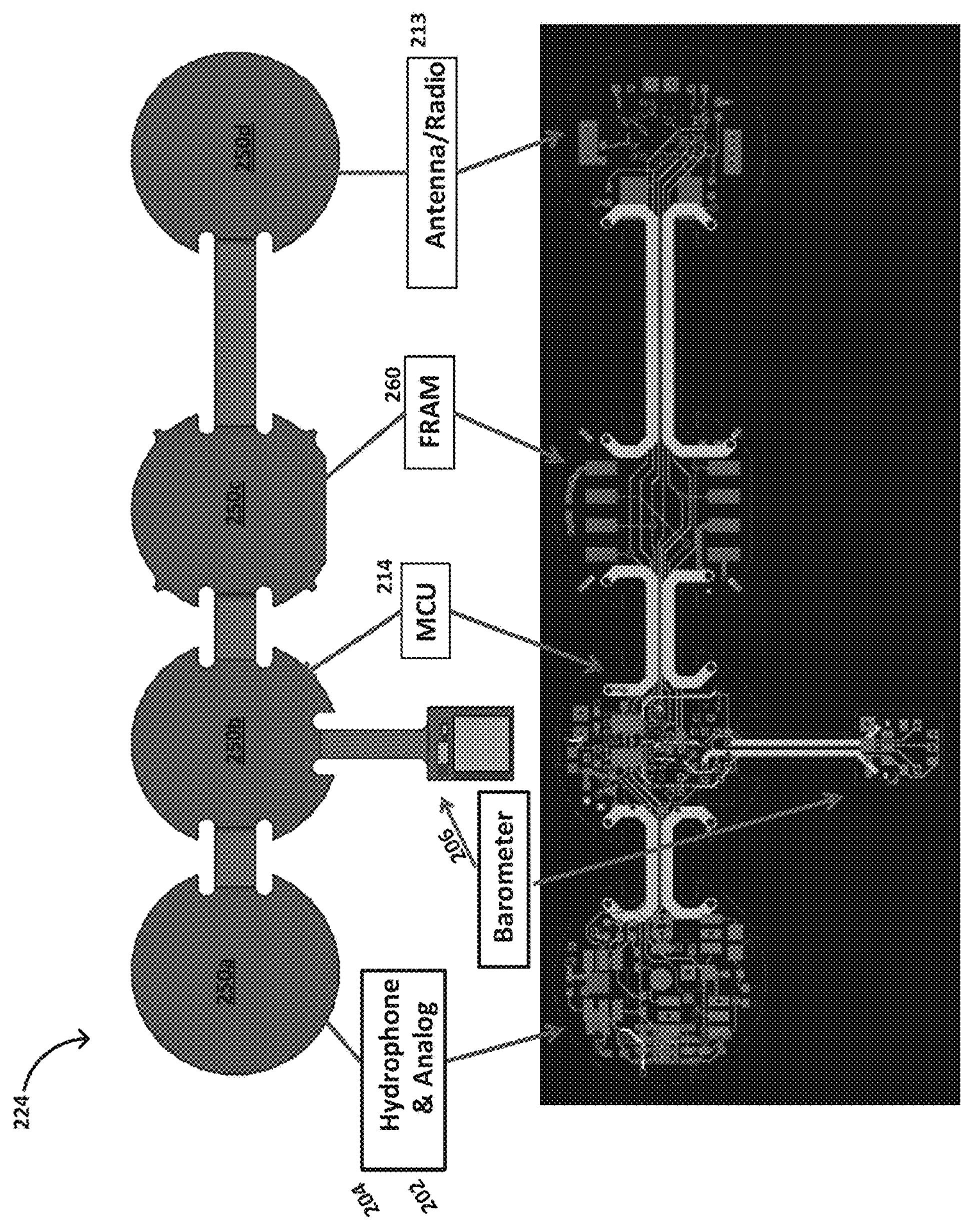
FIG. 2D shows a view of electronic components for the ingestible physiological monitoring device of FIG. 2A on an unfolded printed circuit board.
Figure 2E:
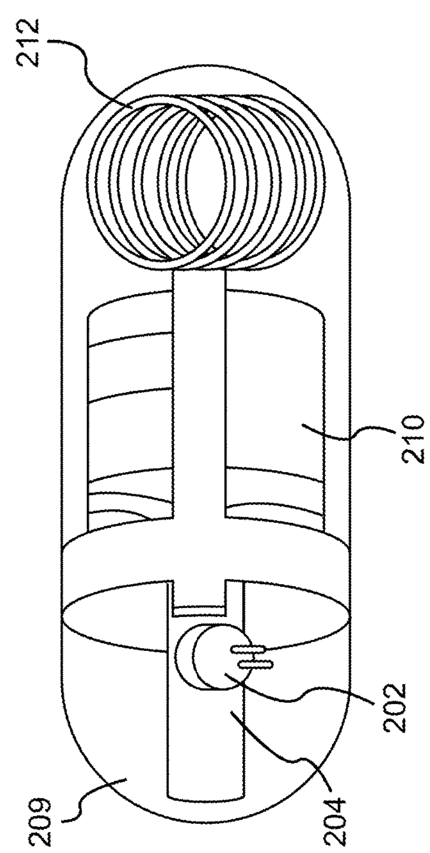
FIG. 2E is a photograph of the ingestible physiological monitoring device of FIG. 2A after encapsulation in a biocompatible silicone housing.

FIGS. 2A-2E illustrate the mechanical assembly and components of another physiological monitoring device 200. FIG. 2A shows the assembled physiological monitoring device 200 before it is encapsulated in a biocompatible silicone housing. FIG. 2B shows the physiological monitoring device 200 without several of the housing pieces. FIG. 2C shows an exploded view of the physiological monitoring device 200. FIG. 2D shows a flexible printed circuit board (PCB) 224, which holds various electronic components, in an unfolded state. And FIG. 2E is a photograph of the ingestible physiological monitoring device after encapsulation in a biocompatible silicone housing.

The physiological monitoring device's electronic components, including a microcontroller unit (MCU) 214, hydrophone 204, thermistor 202, barometer 206, memory 260, and radio 213, are coupled to or mounted on the flexible PCB 224 as shown in FIG. 2D. The flexible PCB 224 is folded as shown in FIGS. 2A-2C, then fit within an electronics housing 208. The PCB 224 can be removably or fixedly coupled to the electronics housing 208 by, for example, gluing, hot welding, a snap-fit mechanism, screws or other fasteners, or by any other suitable coupling mechanism. The electronics housing 208 protects the electronics components from undesired impacts, vibrations, etc.

Together, the folded flexible PCB 224 and electronic housing form a cavity for a battery holder 220 that holds a pair of battery cells 210*a* and 210*b* (collectively, battery cells 210). A plastic spring 211 presses the battery cells 210 and folded flexible PCB 224 together to ensure good electrical connections between the negative and positive terminals of the battery cells 210 and the electronic components mounted or and to the flexible PCB 224. The spring 211 is configured to exert a desired amount of pressure. For example, the spring 211 is configured to exert just enough pressure to push the PCB 224 into the battery 210 for good electrical contact—say, about 2.25 oz at a displacement of about 0.030 inches. However, the spring 211 is also configured not to exert too much force to avoid breaking any of the components while completing the power circuit. The hydrophone 204 is mounted to the flexible PCB 224 on one end of the physiological monitoring device 200 and a loop antenna is mounted to the flexible PCB 224 on the other end of the physiological monitoring device 200. Once assembled, the physiological monitoring device 200 has a diameter of about 10 mm and a length of about 25 mm. Other dimensions are also possible.

FIG. 2D is an illustration of the layout of the flexible PCB 224 while it is unfolded. The flex PCB 224 is a multi-layer printed circuit board that mechanically supports a hydrophone 204, a thermistor 202, a barometer 206 and a loop antenna 212 and electrically connects these components with a microcontroller unit 214 and a FRAM 260. In one embodiment, the flex PCB 224 comprises several disks 250*a*, 250*b*, 250*c*, and 250*d* (collectively, disks 250) which are connected to each other via flexible conductive traces. The hydrophone 204 and the thermistor 202 are fabricated and coupled onto the outermost disk 250*a*. The hydrophone 204 and the thermistor 202 are electrically connected to a microcontroller unit 214 that is embedded on the second disk 250*b*. The barometer 206 is mechanically supported by the second disk 250*b* and is in electrical communication with the microcontroller unit 214 via flexible traces. The third disk 250*c* supports a FRAM 260 that is electrically connected to the microcontroller unit 214 and a loop antenna 212 via traces in or on the PCB 224. The loop antenna 212 and the radio 213 are coupled to the other outermost disk 250*d*. Once the components have been mounted to the PCB 224, the PCB 224 can be folded to fit into the electronics housing 208 as described above and shown in FIGS. 2A and 2C.

The entire assembly shown in FIG. 2A can be vacuum encapsulated in biocompatible silicone (not shown) before ingestion as shown in FIG. 2E. The assembly is inserted into a mold of the biocompatible silicone. The silicone is injected into the mold and allowed to harden. Once the silicone has cured (enough), the mold is removed. In some cases, the entire assembly is encapsulated; in other cases, only a portion of the assembly (e.g., the hydrophone 204) is encapsulated in biocompatible silicone. The silicone protects the device's components, prevents them from leaching materials into the mammal's body.

The housing may also match the acoustic impedance of the hydrophone 204 to the acoustic impedance of the mammal's body, which is roughly the same as the acoustic impedance of water. In some cases, the housing includes or acts as an acoustic impedance-matching layer. This matching layer may have an acoustic impedance of about 2-20 Mrayls (e.g., 2, 4, 6, 8, 10, 12, 14, 16, and 18 Mrayl), which is between the acoustic impedance of soft tissue (about 1.6 Mrayls) and the acoustic impedance of hard piezos like PZT (usually >30 Mrayls). The corresponding thickness of this matching layer depends on its acoustic impedance and the frequencies over which the hydrophone should exhibit sensitivity. A single-frequency, single-layer should have a thickness of about $\lambda/4$, where $\lambda$ is the acoustic wavelength. More complicated, multi-layer structures may also be used.

This physiological monitoring device 200 includes many components that are the same as or similar to the components of the physiological monitoring device 100 shown in FIG. 1A. As readily apparent to one of skill in the art, these components of the physiological monitoring device 200 may perform the same functions and have the same functional relationships as the components of the physiological monitoring device 100 shown in FIG. 1A. For example, the hydrophone 204 collects acoustic signals and transduces them by sensing acoustic energy to electrical signals that ultimately determine heart rate and breathing rate. In some embodiments, the hydrophone is configured to sense acoustic events within a range of about 5 Hz and about 10 kHz. The thermistor 202 measures the body temperature. The barometer measures pressure. Other sensors, such as an acceleration sensor or a pH sensor, can be used to measure other parameters indicative of the mammal's physiological condition. The microcontroller unit 214 processes and optionally analyzes the data received from the hydrophone 204, thermistor 202, and other sensors to determine heart rate, breathing rate, temperature, etc. Further, the microcontroller unit 214 transmits the data to an external data via the radio 213 and the loop antenna 212.

An Acoustic Sensor for a Physiological Monitoring Device

Figures 3A, 3B:
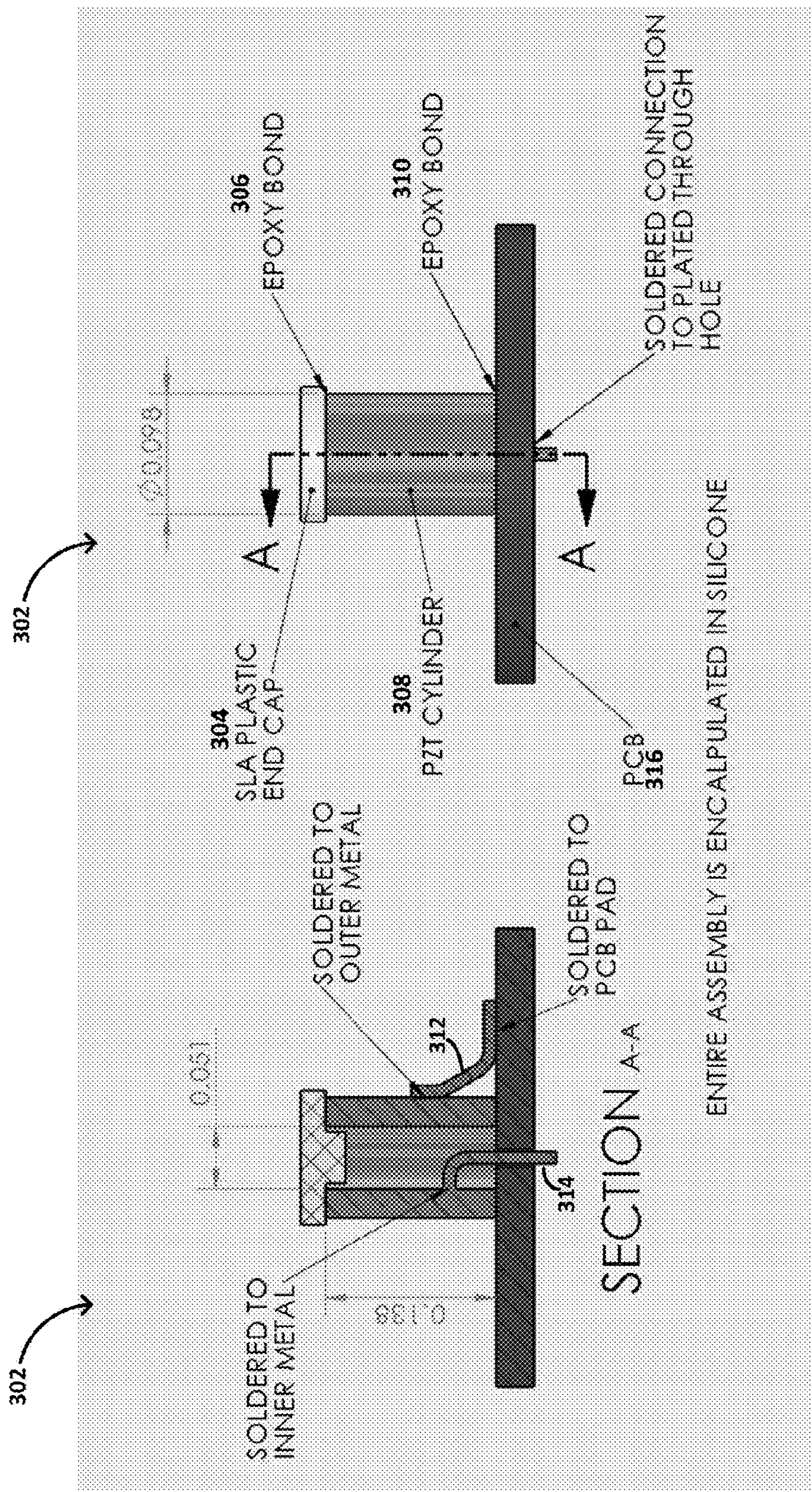
FIG. 3A is a profile view of a hydrophone suitable for use in an ingestible physiological monitoring device.
FIG. 3B is a cutaway view of the hydrophone of FIG. 3A.

FIG. 3A is an illustration of the assembly of a hydrophone 302 suitable for use in the physiological monitoring devices of FIGS. 1A and 2A. The hydrophone includes a hollow piezoelectric (PZT) cylinder 308 coupled on one end to a plastic end cap 304, which comprises a compressible material that allows for external pressure to deform the piezoelectric cylinder 308. The other end of the piezoelectric cylinder 308 is coupled to a PCB 316 (e.g., PCB disk 250*a* in FIG. 2C). The piezoelectric cylinder 308 is coupled to the end cap 304 and PCB 316 using structural adhesives, such as epoxy resins that form epoxy bonds 306 and 310. The epoxy bond 306 couples the piezoelectric cylinder 308 to the end cap 304. The epoxy bond 310 couples the piezoelectric cylinder 308 to the PCB 316. The epoxy bonds 306 and 310 also protect the PCB 316 and the hydrophone 302 from short circuiting and dust.

Strain in the piezoelectric cylinder 308 produces charge that is processed and measured by components on the PCB 316. This charge can measured via two electrical connections to the piezoelectric cylinder 308. The first connection is a wire or conductive trace that is connected on one end to the inside of the cylinder 308 and extends through a hole in the PCB 316. The second connection is a wire or conductive trace that is soldered on one end to the outside of the cylinder 308 and on the other end to a pad on the PCB 316.

TABLE 1 shows a power budget based on the use of two ultra-small coin-cell batteries (377/376 type silver oxide, 24 mAh each) like those shown in FIGS. 2A-2C in the device to provide an expected operational lifetime of four days. This power budget easily allows for continuous physiological status monitoring (PSM) for a non-persistent device design. For persistent devices, a recharging capability could be built into the device, e.g., using an antenna coil for inductively-coupled or wireless resonant recharging. For example, the PSM device may recharged using techniques like those used to recharge cardiac pacemakers. A user would then recharge the device (e.g., twice per week) for continuous operation.

TABLE 1

| Power Budget | | | | | |
|---|---|---|---|---|---|
| | Power Requirements Estimate | | | | |
| | Micro-processor | Microphone, Opamps | Thermistor, Oscillator | Transmitter | Total |
| Nominal Current (uA) | 270 | 160 | 20 | 600 | |
| On time | 100% | 67% | 17% | 17% | |
| Average Current (uA) | 270 | 107.2 | 3.4 | 102 | ~500 uA |

Processing Acoustic Data Acquired with a Physiological Monitoring Device

Figure 4A:
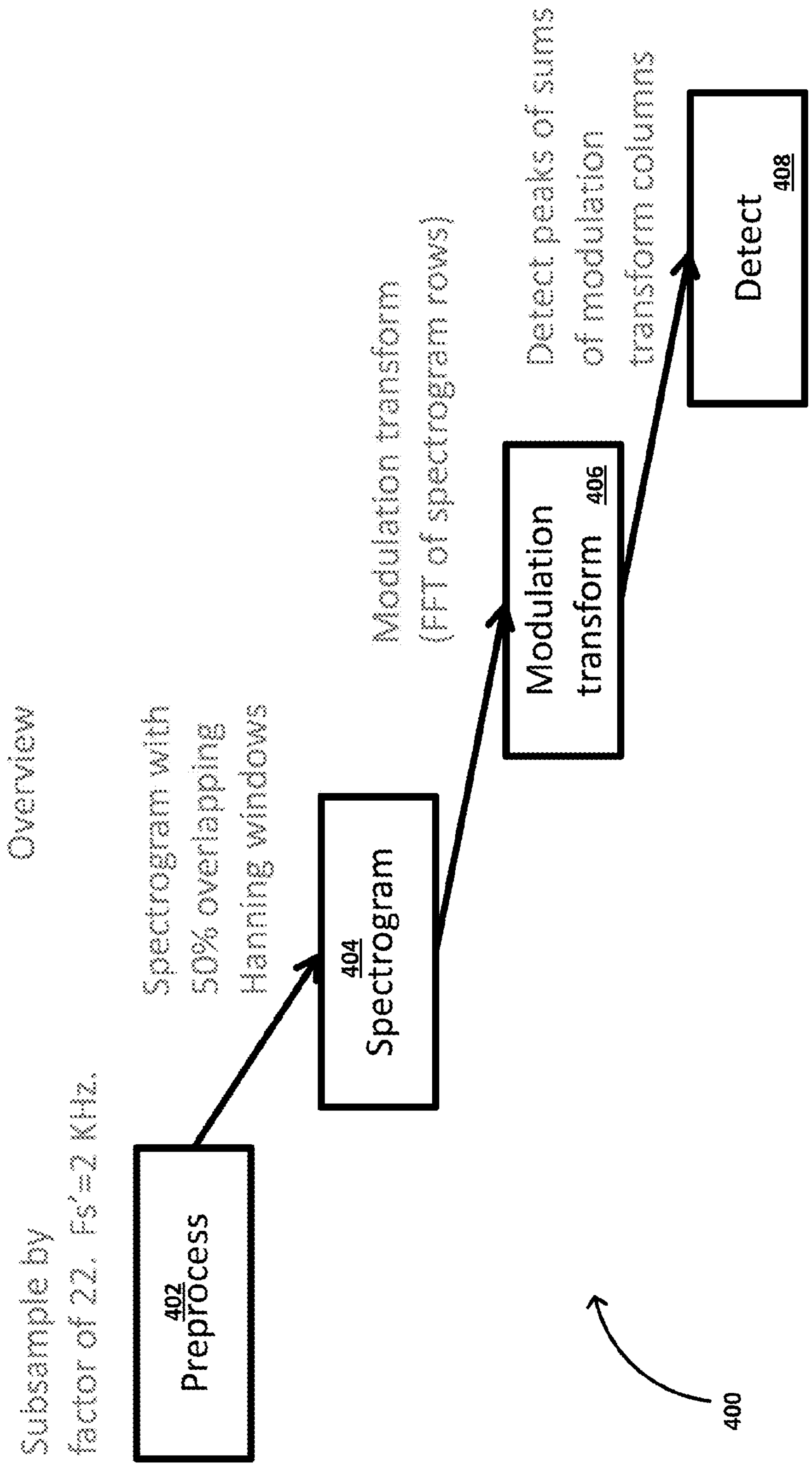
FIGS. 4A-4E illustrate a method for processing acoustic data acquired with a hydrophone or other acoustic sensor in an ingestible physiological monitoring device.

FIG. 4A is a flow diagram illustrating a process 400 for determining heart rate and breathing rate using a physiological monitoring device like the ones shown in FIGS. 1A and 2A. As described above, analog acoustic signals from the hydrophone are digitized by one or more ADCs to produce digitized acoustic signals. In step 402, the microcontroller 120 or the base station preprocess the digitized acoustic signals, e.g., by subsampling them at a predetermined or dynamically determined subsampling factor. In one embodiment, the acoustic signals are sampled at 2 kHz giving a frequency range of 0-1 kHz or less, e.g., 0-500 Hz, 0-250 Hz, etc. This subsampling allows for extracting and determining heart and lung sounds. More specifically, subsampling reduces the data rate, the amount of the data for a given period, or both. Preprocessing may occur as the data are collected (i.e., in real-time) to reduce memory consumption; before the data are transmitted via the radio to the base station to reduce transmission bandwidth, transmission length, or power consumption; when the data is being prepared for further processing; or at any combination of these times.

Figure 4B:
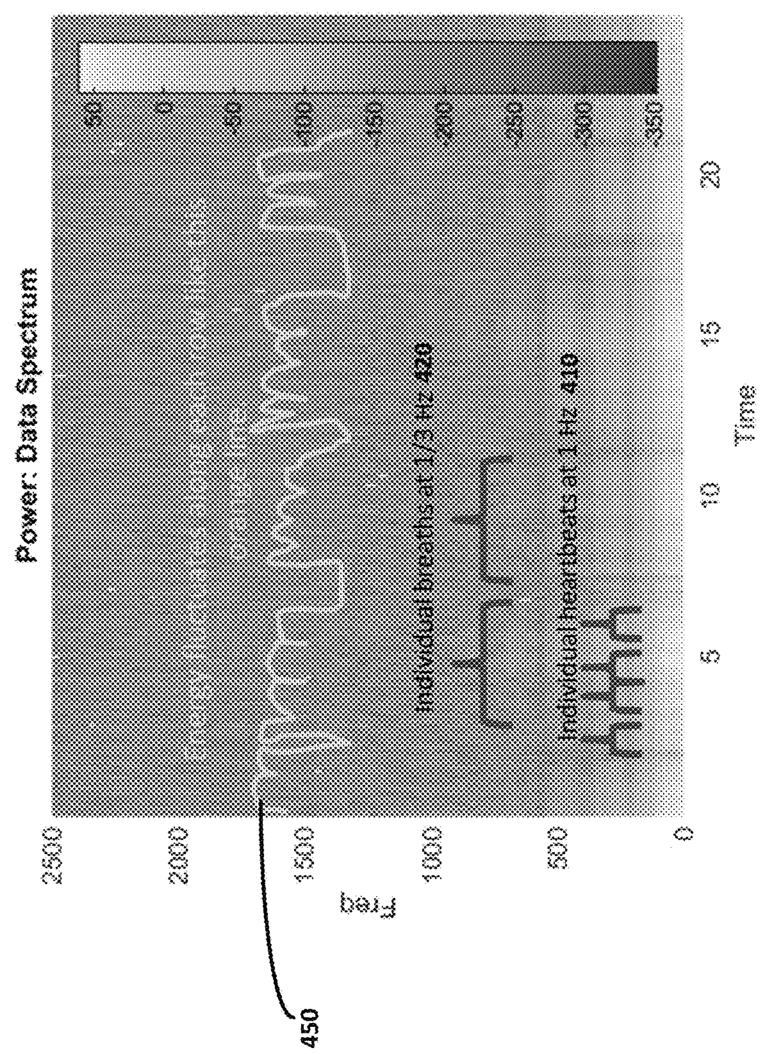

In step 404, the microcontroller or base station generates a spectrogram of the sub sampled data. FIG. 4B shows an example spectrogram, which, as understood by those of skill in the art, represents of the amplitude of a signal in both frequency and time. The mammal's breathing and heart rates appear as time-varying amplitude variations 450 within different spectral bands. In FIG. 4B, with individual heartbeats 410 appearing as lower-frequency traces with a repetition rate of about 1 Hz and individual breaths 420 appearing as higher-frequency traces with a repetition rate of about ⅓ Hz. Energy at some or all of the frequencies shown in the spectrogram change in correlation with heart and breathing sounds. These changes in the amplitudes of different spectral components of the acoustic signals over time provide insights into the breathing and heart rates of the mammal as well as into changes in the breathing and heart rates caused by exertion, stress, illness, etc. Particular patterns may even indicate that the mammal has experienced, is experiencing, or is about to experience a pathological event, such as a cardiac arrhythmia. Other spectral/temporal distributions of acoustic energy may indicate stenosis, chronic obstructive pulmonary disease, asthma, or other conditions that affect the circulatory system or lungs.

Figure 4C:
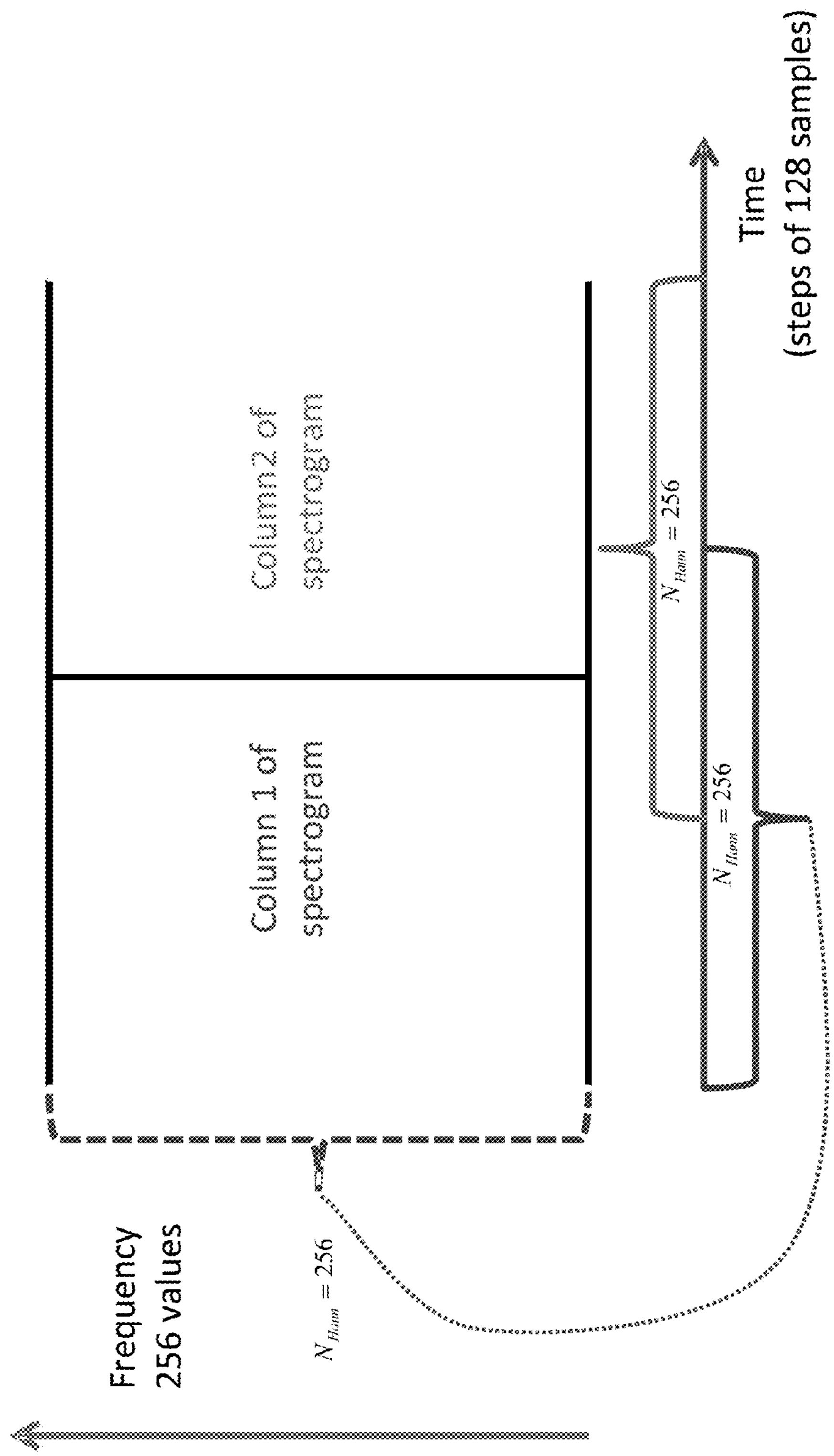

In order to address spectral leakage during spectral analysis, the microcontroller or base station may apply one or more moderate window functions, such as Hanning window functions with 50% overlapping windows, to the data when generating the spectrogram as shown in FIG. 4C. In the case shown in FIG. 4C, the spectrogram contains information at 256 frequency values (spectral bins), so the Hanning windows are chosen to have widths of 256 time-domain samples each and to overlap by 128 time-domain samples. As understood by those of skill in the art, the number of values/samples, the degree of overlap, and the shape(s) of the windows may be adjusted or selected as appropriate.

Figure 4D:
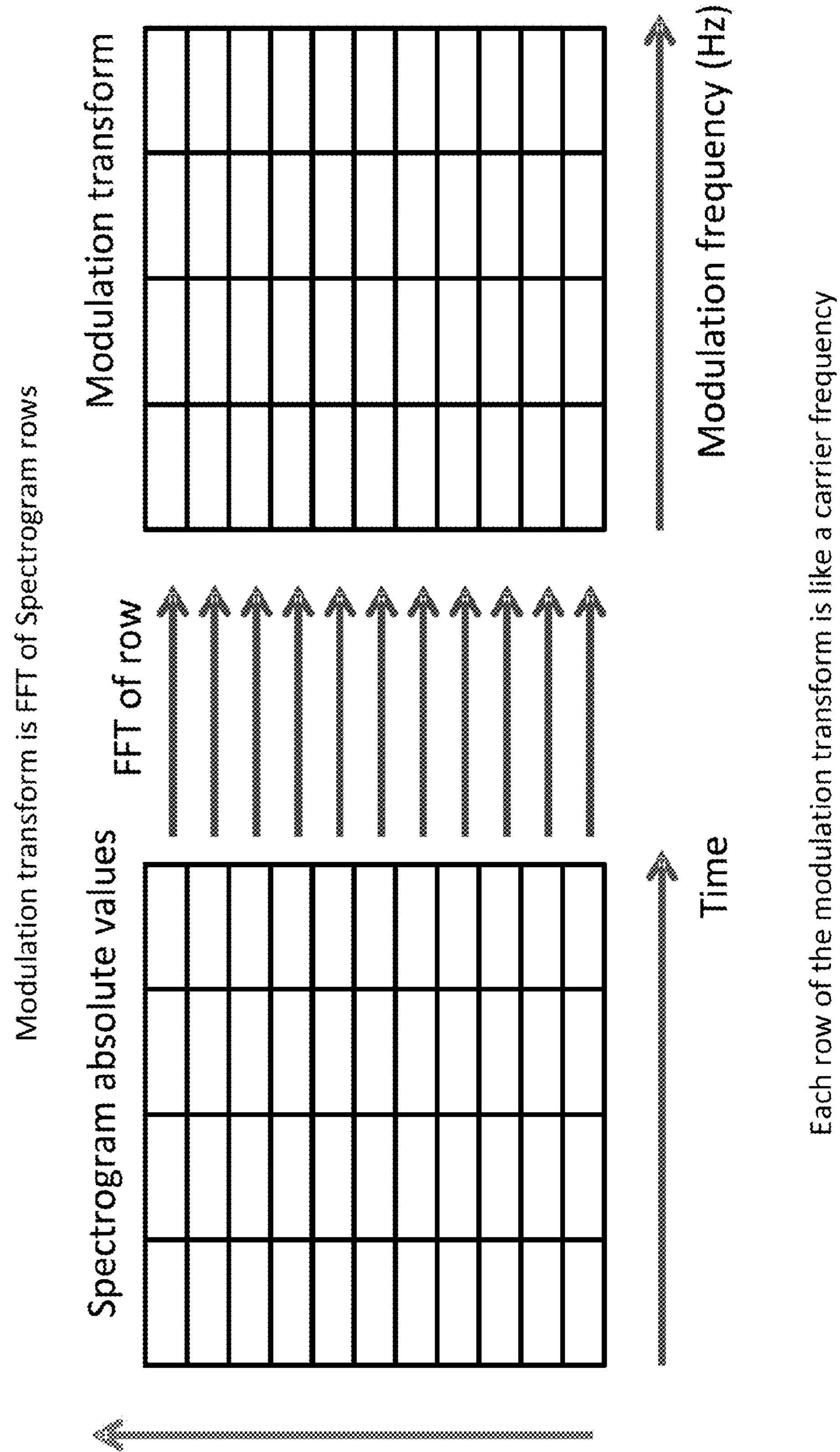

In step 406, the microcontroller or base station performs a modulation transform 406 on the spectrogram. More specifically, the microcontroller or base station performs an FFT of each row (time series) in the spectrogram as shown in FIG. 4D. These FFTs transform the acoustic data from time domain to frequency domain. Each row of the resulting modulation transform is like a carrier frequency.

Figure 4E:
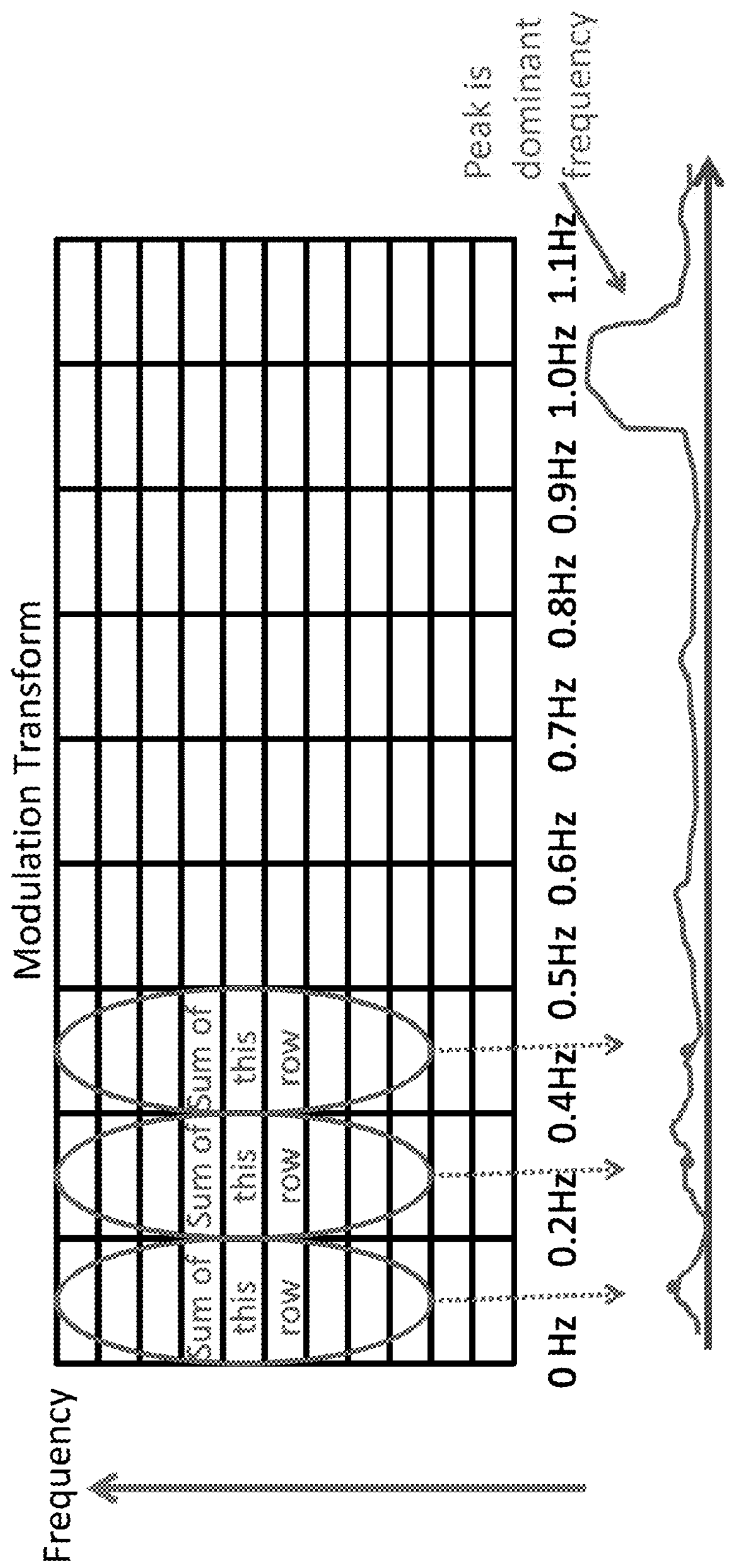

In step 408, the microcontroller or base station sums the non-ballistic frequencies in each column (spectral series) of the modulation transform. Subtracting the mean yields a trace that shows peaks at different modulation frequencies as shown in FIG. 4E. The larger peaks correspond to dominant frequencies. For acoustic data collected by an exemplary physiological monitoring device, the peaks represent the heart and breathing rates.

Experimental Evaluation of a Physiological Monitoring Device

The following paragraphs disclose initial proof-of-concept experiments in a porcine model to show that HR and BR can be measured simultaneously and with high fidelity from within the GI tract using a single acoustic waveform. Using an endoscopically-guided miniature electret microphone, acoustic data was measured along the GI tract from the mouth to the colon. The impact of device contact with GI tissue and previously ingested food on acoustic data acquisition was evaluated. Then, a robust signal-processing algorithm to analyze the raw waveforms was developed. The results thus obtained support that an ingestible ultra-miniature device could accurately measure vital signs. This technology is likely to be adaptable to a wide range of clinical and non-clinical uses.

Physiological monitoring experiments were performed in two sedated Yorkshire pigs using an endoscopically-guided electret microphone to collect acoustic waveforms along the GI tract. Physiological waveforms using a standard veterinary vital signs monitor, including external 3-lead ECG, PPG, capnography (via expired breath $CO_2$ analysis), and a superficial microphone positioned directly above the heart were concurrently recorded. A total of 262 minutes of HR and 263 minutes of BR data were collected from all segments of GI tract over the course of four experimental days in two Yorkshire pigs. Specifically, 59.7, 44.7, 84.3, 33.7 and 40.3 minutes of raw audio data were collected from the oral cavity, esophagus, stomach, proximal duodenum and rectum respectively.

Figure 5:
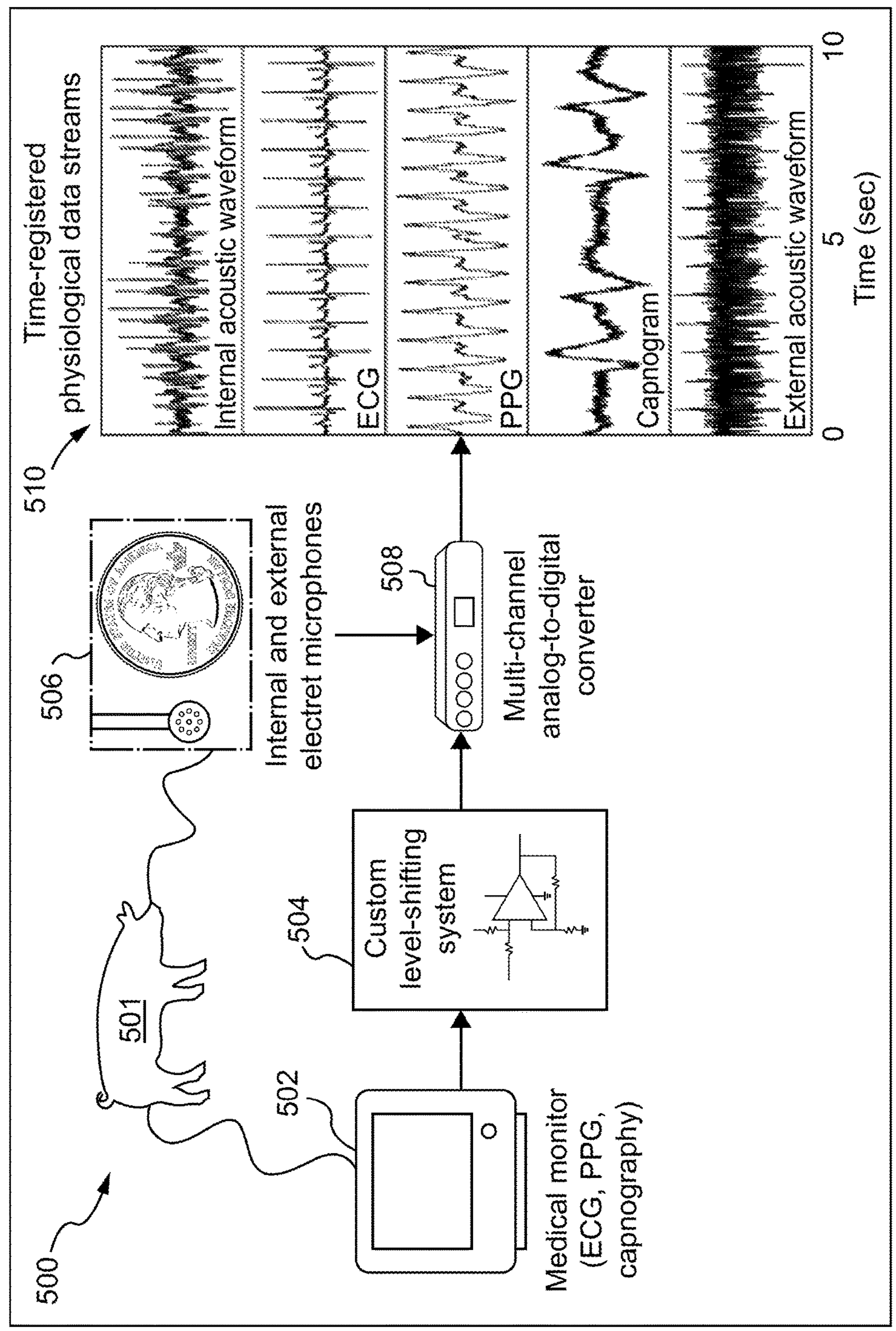
FIG. 5 illustrates an experimental setup for acquiring and processing acoustic data to yield heart rate and breathing rate of a porcine model.

FIG. 5 is a schematic representation of the experimental setup 500 and the representative dataset. The animal model 501 is anesthetized and attached to a medical monitoring system 502 that measures ECG, capnography, and photoplethysmography (PPG) waveforms simultaneously. A custom voltage level-shifting circuit 504 for each waveform is built, which outputs to a commercial ADC 508. Two electret microphones 506, one controlled internally by the endoscope, the other attached superficially on the pig's chest just above the heart, send data to the ADC 508. The final result is perfectly time-registered data streams 510 for heart and lung function, as well as the acoustic waveforms. Example concurrent physiological data measurements were taken from the proximal third of a porcine stomach including the acoustic waveform from our internal electret microphone, ECG, photoplethysmography (PPG) which indicates systemic oxygen perfusion levels, capnography from expired $CO_2$ content, and the acoustic waveform from the external microphone positioned above the heart. (Note that the raw PPG data from the SurgiVet system seems to be inverted, and the raw capnography data appears to be the flow rate of $CO_2$, thus giving a first derivative of the more familiar capnogram waveform.)

Raw waveforms were processed using a phonocardiogram HR estimation algorithm modified to enable simultaneous extraction of HR and BR from a single raw waveform and with processing steps simple enough to be implemented on a microcontroller (such as a Texas Instruments MSP430). The raw waveform is split and copied into a HR and BR track, and each is processed with parameters characteristic of each signal as further illustrated in FIG. 6. The first processing stage consists of an analog front end, namely resistor-capacitor (RC) based bandpass (for FIR) and low-pass (for BR) filters. A bandpass filter from 10-45 Hz was chosen for the HR and a low-pass filter at 5 Hz for BR; these values were chosen to maximize the non-overlapping signal for each respective vital sign while both being well below the fundamental frequency for human vocalization (~85 Hz). The second and third stages increase the signal-to-noise ratio (SNR) by successively computing the signal's energy and its average magnitude difference function (AMDF), which is a relatively simple auto-correlation function. (Other auto-correlation functions may be used as well.) The final stage uses a robust valley-detection algorithm for estimation of the HR and the BR from the AMDF. All processing disclosed herein were performed on non-overlapping 20-second data frames during which a single average HR and BR is reported. A 20-second frame duration was chosen as a compromise between reduced latency and a sufficient window length to encompass more than one breath. There were 787 and 788 total HR and BR frames, respectively.

Figure 6:
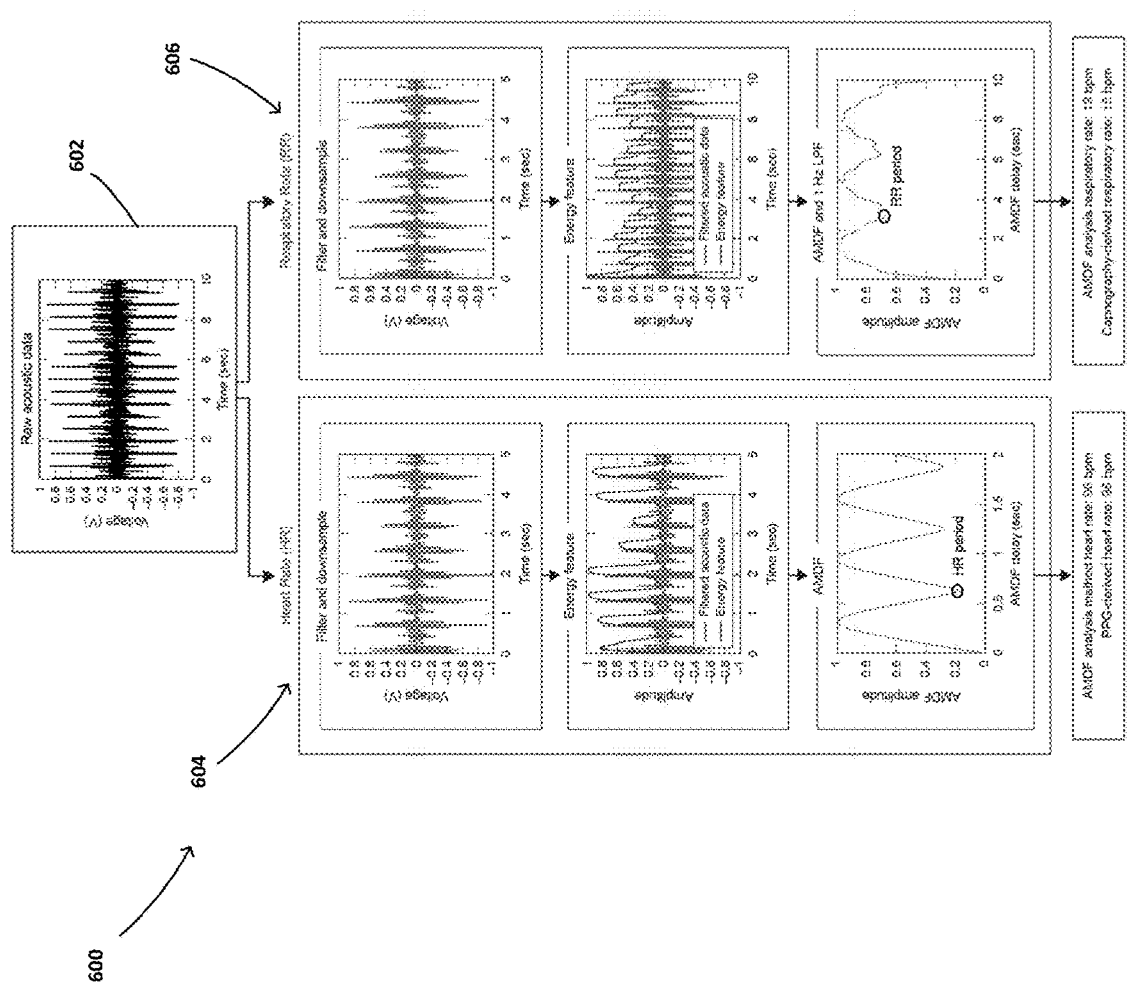
FIG. 6 illustrates processing experimentally acquired acoustic data to yield heart rate and breathing rate.

FIG. 6 is a schematic processing flow chart 600 for HR and BR estimation from internal microphone data 602. The signal is copied into a HR track 604 and a BR track 606 and then analog filtered and down-sampled. A sliding window computes an energy feature that is input to the average magnitude difference function (AMDF). The first valley of the AMDF is the estimated vital sign.

Figure 7:
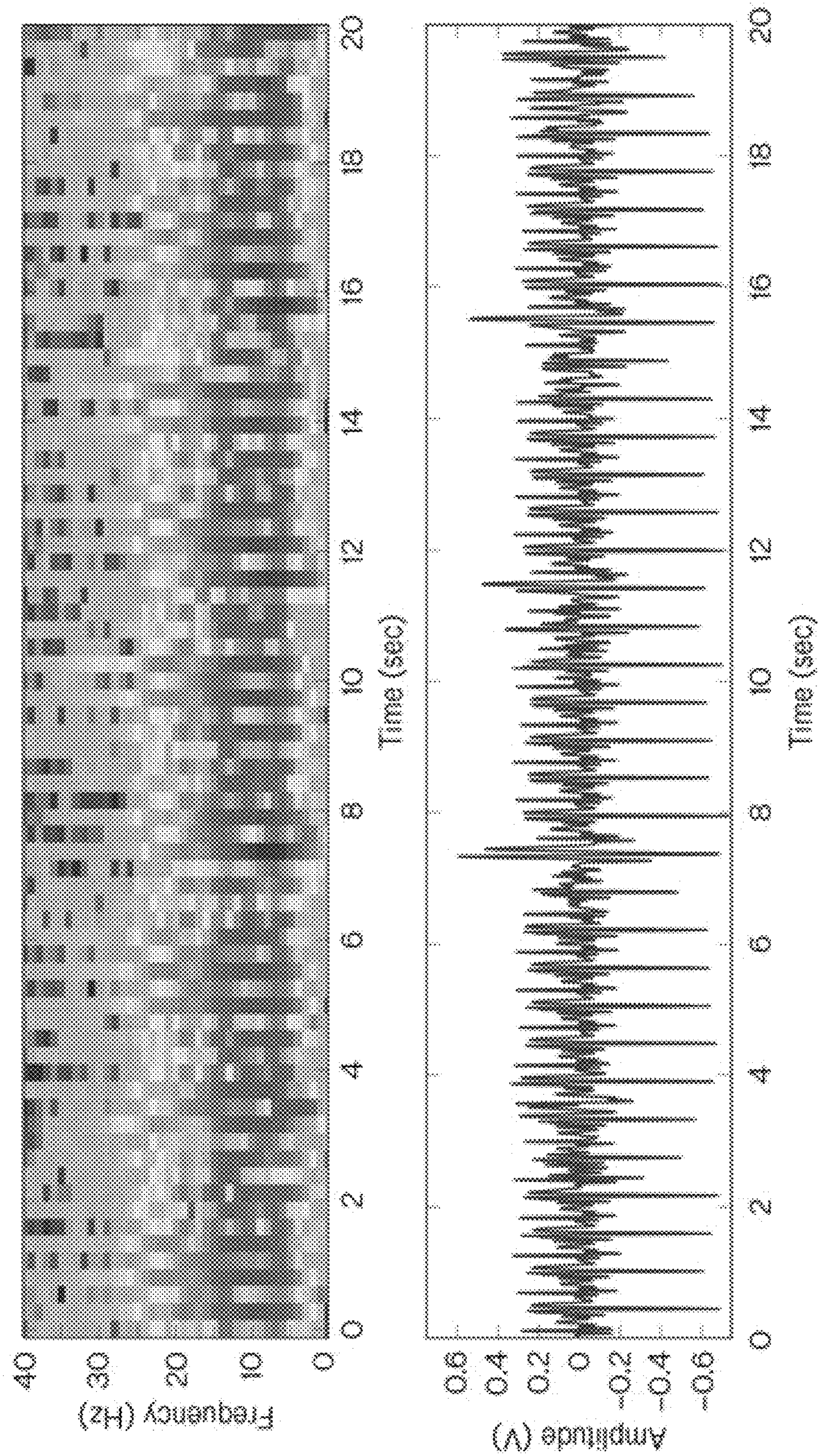
FIG. 7 shows a spectrogram (top) and time-domain trace (bottom) of experimentally acquired acoustic data.

FIG. 7 is an example spectrogram and corresponding time course data of the internal acoustic signal measured in the esophagus. A majority of the HR signal energy is within 10-45 Hz, and the BR signal energy below 5 Hz. These values are also below the fundamental frequency for human vocalization, ensuring speech will not contribute to vital sign signal noise.

HR and BR concordance with external ECG and capnography is very strong in the esophagus, stomach, and duodenum: the HR is detected within 5 bpm >94%, 93%, 82% of the time, respectively. The BR is detected >75% of the time within 5 breaths per minute in these respective locations. While an acoustic waveform in the mouth and colon was measured, agreement with standard vital sign monitoring was poor. However, this can be overcome by conducting additional non-linear check on reported estimates such as running median filter, or a more sophisticated AMDF/valley finding such as the extended AMDF.

Figure 8:
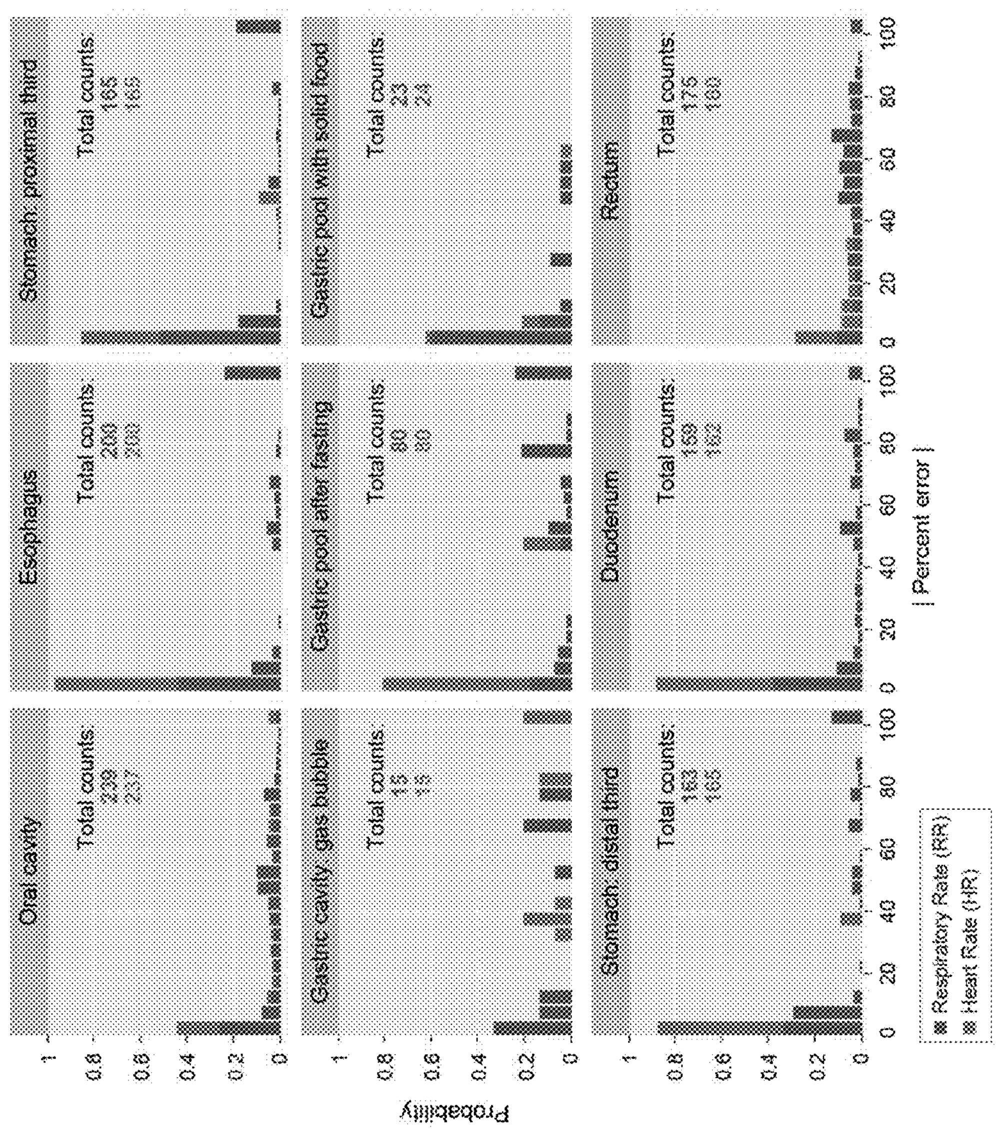
FIG. 8 shows histograms of breathing rates (BRs) and heart rates (HRs) at different locations in the gastrointestinal tract of the porcine model.

FIG. 8 represents HR and BR estimation performance histograms for all data collected as a function of anatomical location. The "Total Counts" for each location is the number of non-overlapping 20 s frames collected to build the histogram. The AMDF peak-finding algorithm can trigger upon higher-order harmonics of the fundamental period, giving percent errors concentrated at 50 and 100%; these errors can be easily addressed with more sophisticated AMDF algorithms or running median filters.

The Percent error histograms as illustrated in FIG. 8 show similar empirical distributions among anatomical locations when there are sufficient samples. Namely, measurement error is concentrated near 0%, 50%, and 100%. This consistent and repeatable distribution results from the AMDF valley-finding algorithm triggering on incorrect valleys due to noise. With no noise, the first AMDF function valley represents the fundamental period of the heart rate or breathing rate; however, there are additional valleys at multiples of this fundamental period due to the periodicity of the signal, as well as spurious smaller valleys due to noise. Higher-order integer harmonic valleys thus yield percent errors of 50 or 100%. Any detections on spurious valleys before the first true valley result in over estimations of the parameter of interest; if these estimates occur at less than half the true period, the error value becomes >100%, which are clustered together in FIG. 8. The harmonic nature of the AMDF function and its corresponding error modes are a recognized failing of parameter estimation from a periodic waveform such as the AMDF. Potential improvements in future work include an additional non-linear check on reported estimates such as a running median filter, or a more sophisticated AMDF/valley finding such as the Extended AMDF.

Vital Sign Monitoring in Heterogeneous GI Environments

An ingestible monitoring device must be able to function under a variety of common GI environmental conditions consistent with the fasted and fed states. To demonstrate the system's applicability to these heterogeneous GI environments, the system was used to measure waveforms in the gastric content (either solid, liquid, or in a gas bubble, for a total of 39.7 minutes of data collected from the six animals), and in contact with the gastric wall (approximately 110 minutes of data collected from the six animals, both in the proximal and distal thirds of the stomach). All these areas demonstrated HR and BR values in good agreement with external VS monitor values. The HR median percent error was noted in the proximal third, a gas bubble, gastric pool and distal third as 5.88%, 0%, 0%, and 0%, respectively. For BR, the median percent error was 0% in the proximal third, gas bubble, gastric pool and distal third. Additional median percent errors are further noted in FIG. 9.

Figure 9:
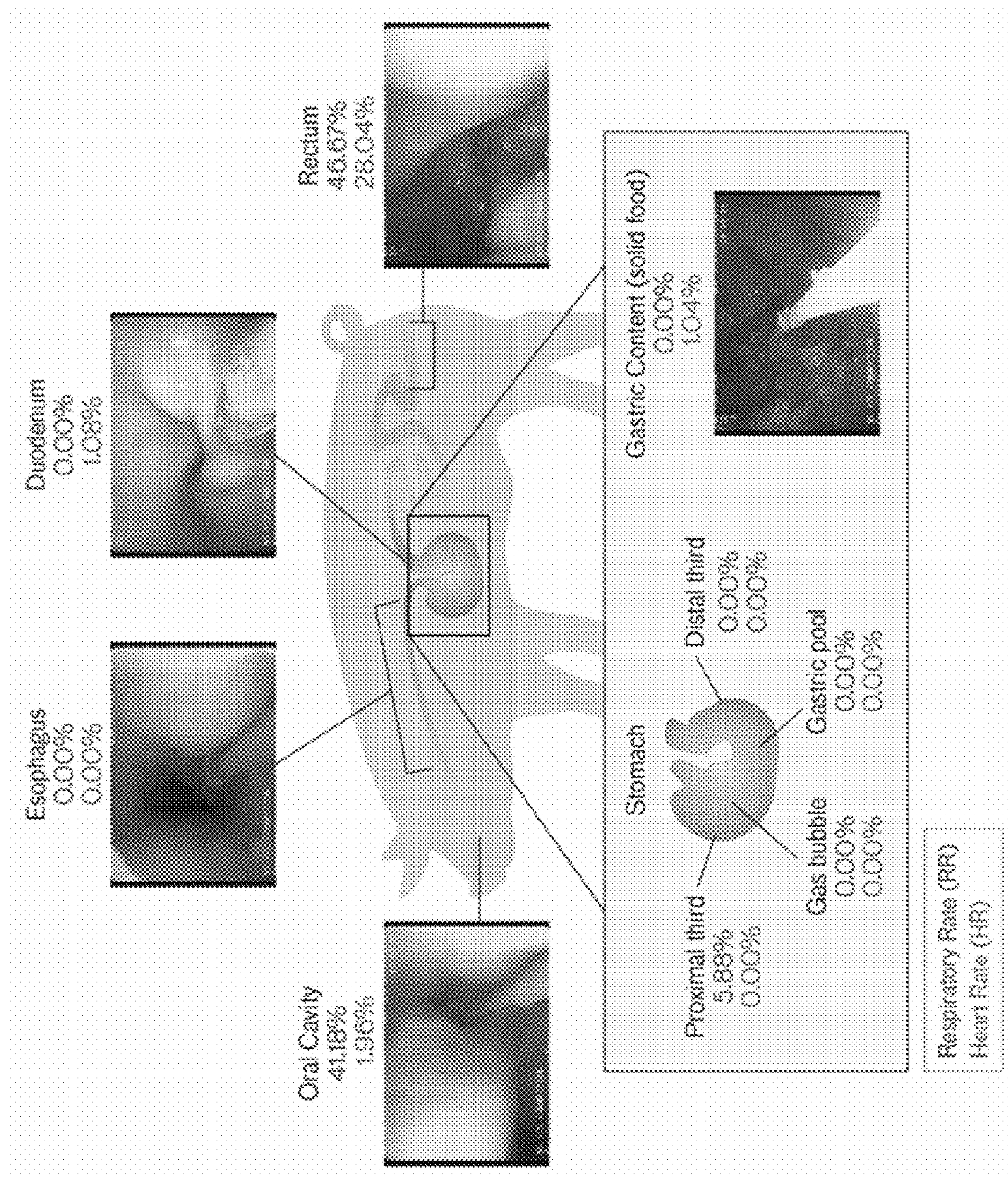
FIG. 9 illustrates acoustic data acquisition locations within the gastrointestinal tract of the porcine model.

FIG. 9 is an illustration of measurement sites and the median percentage error between ECG and capnography derived HR and BR and internally derived HR and BR data (via our phonocardiogram/average magnitude difference function analysis).

Porcine Model Sign Monitoring Experiments

In vivo porcine studies were performed in 6 Yorkshire pigs weighing approximately 65 kg. For evaluations free of food material the pigs received a liquid diet for 48 hours prior to the procedure. Otherwise animals were fasted overnight. On the day of the procedure, the morning feed was held and the animal was sedated and intubated. Following induction of anesthesia with intramuscular injection of Telazol (tiletamine/zolazepam) 5 mg/kg, xylazine 2 mg/kg, and atropine 0.05 mg/kg, the pigs were intubated and maintained on isoflurane 1-3%. An endoscope guiding a miniature electret microphone (PUI Audio, part #POM-2245L-C10-R) was introduced in the esophagus and recordings taken from the mouth, esophagus, stomach, and duodenum with and without tissue contact. Additionally an enema was performed and recordings were taken from the colon. All procedures were conducted in accordance with protocols approved by the Massachusetts Institute of Technology Committee on Animal Care.

Raw acoustic data was sampled at 44.1 kHz. A custom level-shifting device (shifting from 0-5 V to 0-1.6 V) capable of interfacing with existing medical monitoring equipment attached to the animal (Surgivet Advisor™, Smiths Medical) and with a multi-channel ADC (Roland Octa-Capture™) capable of handling all 5 input streams (ECG, PPG, capnography, internal and external electret microphones) and outputting via a USB connection to a laptop running Audacity audio collection software was built.

Signal Processing

The algorithm was specifically designed for implementation in a low size, weight, and power device. First, the 44.1 kHz signal was copied into two parallel processing tracks; one track ultimately estimates HR, and the other RR. The signal in the HR tract is filtered with an analog RC bandpass filter constructed from a low pass filter with a 3 dB cutoff frequency at 65 Hz and a high pass filter with a 3 dB cutoff frequency at 25 Hz. The signal in the BR tract is filtered with a second order analog RC low pass filter with a 3 dB cutoff frequency at 5 Hz. Both signals are then decimated by a factor of 450 to a sampling rate of 98 Hz to emulate minimal data storage and processing capabilities.

The analog filtered signal, x[n], is normalized to maximum amplitude of −1 or 1 and is denoted $x[n]_{norm}$. Then, a sliding window over the 20 second frame computes the energy, E[n] according to Equation 1 below. The HR track uses a window of $N_{window}$=25 samples or approximately 0.25 seconds, and the BR track uses a window of $N_{window}$=196 samples or 2 seconds.

$$E = \frac{1}{N_{window}} \cdot \sum_{k=1}^{N_{window}} (x_{norm}[k])^2 \qquad (1)$$

Equation 1 represents energy feature calculation. The average magnitude difference function (AMDF) computes a waveform D[n] similar to the output from an autocorrelation operation, but without using any multiplications. Therefore, it was chosen over the autocorrelation technique in anticipation of implementing the estimation algorithm in ultra-low power and size hardware. The AMDF slides the signal over itself and computes the average difference between the overlapped segments (Equation 2). When the two segments are similar, the AMDF outputs a low value, and when they are dissimilar, the AMDF outputs a high value. The AMDF increases the signal to noise ratio by exploiting the periodicity of the HR and the BR waveforms over the frame. $N_E$ is the number of samples in the frame of the energy signal. $N_E$ is 1960 samples which corresponds to 20 seconds. d varies from 0 to 196 (2 seconds) or 0 to 980 (10 seconds) for the HR or BR estimation because normal beating and respiration have periods less than these upper bounds.

$$N = N_E - d; \qquad (2)$$

$$D[d] = \frac{1}{N} \cdot \sum_{k=0}^{N} |E[k] - E[k+d]|$$

Equation 2 represents average magnitude difference function. The final stage in each track is the estimation of the HR and RR from the AMDF function. The vital sign estimation reduces to a valley-detection-in-noise problem because the true HR or BR will be the first significant dip at which the AMDF becomes close to zero not counting the AMDF value at zero lag. (The zero lag position has an AMDF value of exactly zero because the two segments being subtracted are identical.) As the segments slide over each, the heart beat or breath that was well aligned in each segment becomes misaligned, and the AMDF value increases. However, eventually the segments will have slid far enough apart that the original heart beat or breath will overlap with the second heart beat or breath in the frame. Because of the consistency in heart rate and breath morphology as an output from the energy stage, the AMDF function will compute a small, non-zero value before increasing once again. If several heart beats are within a frame, the AMDF function will appear to have a ripple or sinusoidal pattern as the first heart beat overlaps each of the successive heart beats. The period of the ripple is the period of the vital sign to be estimated.

The signal processing disclosed produces accurate HR and BR estimates for the majority of the GI tract. Overall performance is very strong in the esophagus, stomach, and duodenum: HR is detected within 5 bpm >94%, 93%, 82% of the time, respectively. The BR is detected >75% of the time within 5 breaths per minute in these respective locations. Measurements of an acoustic waveform in the mouth and colon did not agree well with standard vital sign monitoring. Because of the excellent performance of the sensor and algorithm proximal to the heart and lungs, these sites may have been too distant from the signal source for the sensitivity of the particular microphone chosen (−45 dB±4 dB). Higher sensitivity electret or MEMS microphones may be chosen, but they should be small enough for ingestion and have sufficiently low frequency sensitivity (<5 Hz for RR, and between 25 and 45 Hz for the HR).

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An ingestible device for monitoring a physiological status of a mammal, the ingestible device comprising:

a biocompatible housing;

an acoustic sensor, disposed within the biocompatible housing, to transduce acoustic waves propagating within the mammal into an analog signal, the acoustic waves being at frequencies within a range of about 5 Hz and about 10 kHz;

an analog-to-digital converter (ADC), disposed within the biocompatible housing and operably coupled to the acoustic sensor, to generate a digital representation of the analog signal;

a processing unit, disposed within the biocompatible housing and operably coupled to the ADC, to store the digital representation;

a radio, disposed within the biocompatible housing and operably coupled to the processing unit, to transmit the digital representation to a base station disposed outside the mammal; and a power supply to provide electrical power to at least one of the acoustic sensor, the ADC, the processing unit, or the radio.

2. The ingestible device of claim 1, wherein the biocompatible housing has an acoustic impedance of about 2 Mrayls to about 20 Mrayls.

3. The ingestible device of claim 1, wherein the biocompatible housing has a length of less than about 3 cm and a diameter of less than about 1 cm.

4. The ingestible device of claim 1, wherein the biocompatible housing has a length of less than about 2 cm.

5. The ingestible device of claim 1, wherein the processing unit is configured to form at least one of an estimate of a heart rate of the mammal, an estimate of a breathing rate of the mammal, or an indication of a pathological event of the mammal based on the digital representation.

6. The ingestible device of claim 1, wherein the radio is configured to transmit the digital representation to the base station and to receive a signal from the base station.

7. The ingestible device of claim 6, wherein the processing unit is configured to trigger data collection by the acoustic sensor in response to the signal.

8. The ingestible device of claim 1, further comprising:

a low-pass filter, disposed within the biocompatible housing and operably coupled to the acoustic sensor and the ADC, to filter the analog signal prior to generation of the digital representation of the analog signal.

9. The ingestible device of claim 8, wherein the processing unit is configured to estimate a breathing rate of the mammal based on the digital representation.

10. The ingestible device of claim 1, further comprising:

a band-pass filter, disposed within the biocompatible housing and operably coupled to the acoustic sensor and the ADC, to filter the analog signal prior to generation of the digital representation of the analog signal.

11. The ingestible device of claim 10, wherein the processing unit is configured to estimate at least one of a heart rate or heart rhythm of the mammal based on the digital representation.

12. The ingestible device of claim 1, further comprising:

a temperature sensor, disposed within the biocompatible housing, to sense a temperature of the mammal.

13. The ingestible device of claim 1, further comprising:

an accelerometer, disposed within the biocompatible housing and operably coupled to the processing unit, to sense acceleration of the ingestible device and to provide an acceleration signal representative of the acceleration of the ingestible device to the processing unit.

14. The ingestible device of claim 13, wherein the processing unit is configured to estimate at least one of motion of the ingestible device or motion of the mammal based on the acceleration signal.

15. The ingestible device of claim 1, further comprising:

a pressure sensor, disposed within the biocompatible housing and operably coupled to the processing unit, to sense a change in pressure relating to at least one of motion separation, smooth muscle functionality, gastrointestinal transit time, or an inflammatory condition.

16. A method of monitoring a physiological status of a mammal, the method comprising:

transducing, with an acoustic sensor disposed within an ingestible pill ingested by the mammal, at least one acoustic wave propagating within the mammal into an analog signal, the at least one acoustic wave being at a frequency within a range of about 5 Hz and about 10 kHz;

generating, with an analog-to-digital controller (ADC) operably coupled to the acoustic sensor, a digital representation of the analog signal; and estimating at least one of a heart rate of the mammal, a breathing rate of the mammal, or an indication of a pathological event of the mammal based on the digital representation.

17. The method of claim 16, wherein estimating the at least one of the heart rate of the mammal, the breathing rate of the mammal, or the indication of a pathological event of the mammal comprises:

sub sampling the digital representation to produce a subsampled digital representation;

generating a spectrogram of the subsampled digital representation;

producing a modulation transform of the spectrogram; and analyzing a distribution of energy in the modulation transform.

18. The method of claim 16, wherein estimating the at least one of the heart rate of the mammal, the breathing rate of the mammal, or the indication of a pathological event of the mammal comprises:

filtering the analog signal with a low-pass filter prior to generation of the digital representation of the analog signal; and estimating the breathing rate based on the digital representation of the analog signal.

19. The method of claim 16, further comprising:

filtering the analog signal with a band-pass filter prior to generation of the digital representation of the analog signal; and estimating the heart rate based on the digital representation of the analog signal.

20. The method of claim 16, wherein estimating the at least one of the heart rate of the mammal, the breathing rate of the mammal, or the indication of a pathological event of the mammal comprises:

filtering at least one of the analog signal or the digital representation with a matched filter corresponding to an acoustic signature of at least one pathological event.

21. The method of claim 16, wherein the at least one pathological event comprises at least one of a cardiac arrhythmia, stenosis, chronic obstructive pulmonary disease, or asthma.

22. The method of claim 16, further comprising:

transmitting an indication of the at least one pathological event to a receiver disposed outside of the mammal.

23. An ingestible device for monitoring a physiological status of a mammal, the ingestible device comprising:

a biocompatible dielectric material having an acoustic impedance of about 2 Mrayls to about 20 Mrayls;

a hydrophone, encapsulated within the biocompatible dielectric material, to acquire acoustic data within a frequency range of about 5 Hz to about 10 kHz;

a first filter, operably coupled to the hydrophone, to generate a first filtered analog signal from the acoustic data;

a second filter, operably coupled to the hydrophone, to generate a second filtered analog signal from the acoustic data;

a first analog-to-digital converter (ADC), operably coupled to the first filter, to generate a first digital signal from the first filtered analog signal;

a second ADC, operably coupled to the second filter, to generate a second digital signal from the second filtered analog signal;

a processor, operably coupled to the first ADC and the second ADC, to estimate a heart rate of the mammal from the first digital signal and a breathing rate of the mammal from the second digital signal; and a radio, operably coupled to the processor, to transmit the heart rate and the breathing rate to an external wireless device disposed outside the mammal power supply.

* * * * *